US010081843B2

(12) United States Patent
Stahl et al.

(10) Patent No.: US 10,081,843 B2
(45) Date of Patent: *Sep. 25, 2018

(54) USE OF BIRTHING MANURE TO SCREEN FOR PATHOGENIC INFECTION IN FARMED ANIMALS

(76) Inventors: Mark Stahl, Sunbury, PA (US); John Stahl, Sunbury, PA (US); Richard Stahl, Sunbury, PA (US)

( * ) Notice: Subject to any disclaimer, the term of this patent is extended or adjusted under 35 U.S.C. 154(b) by 281 days.

This patent is subject to a terminal disclaimer.

(21) Appl. No.: 12/856,434

(22) Filed: Aug. 13, 2010

(65) Prior Publication Data

US 2011/0086351 A1 Apr. 14, 2011

Related U.S. Application Data

(60) Provisional application No. 61/274,828, filed on Aug. 21, 2009, provisional application No. 61/274,829, filed on Aug. 21, 2009, provisional application No. 61/286,885, filed on Dec. 16, 2009.

(51) Int. Cl.
*C12P 19/34* (2006.01)
*C12Q 1/70* (2006.01)

(52) U.S. Cl.
CPC .................................... *C12Q 1/701* (2013.01)

(58) Field of Classification Search
USPC ................................................ 435/6.12, 91.2
See application file for complete search history.

(56) References Cited

U.S. PATENT DOCUMENTS

| | | | | |
|---|---|---|---|---|
| 7,569,367 B2 * | 8/2009 | Knoll et al. | ................. | 435/91.2 |
| 2004/0185488 A1 * | 9/2004 | Buergelt et al. | .................. | 435/6 |
| 2007/0042408 A1 * | 2/2007 | Knoll et al. | ...................... | 435/6 |

OTHER PUBLICATIONS

Knuuttila et al., Veterinary Microbiology 133, 229-238 (Jan. 2009).*
Olofsson et al., J. Clin. Micro. 37(12), 4145-414149 (1999).*
Gottschalck et al., J. Virology 65(8), 4378-4386 (1991).*
Bloom et al., Scientifur 21(2), 141-146 (1997).*
Jackson et al., Am. J. Vet. Res. 57, 1753-1758 (1996).*
Oie et al., J. Virology 70(2), 852-861 (1996).*

* cited by examiner

*Primary Examiner* — Kenneth R Horlick
(74) *Attorney, Agent, or Firm* — Laurence Weinberger

(57) ABSTRACT

Animal husbandry has always been susceptible to the ravages of pathogenic infections. Poultry flus and cattle diseases are but two examples that have dire consequences for animals and adversely affect the economic fortunes of farmers. A testing and culling methodology is presented that can eliminate pathogens from an infected herd. The sensitivity of PCR to detect very low levels of nucleic acid of an infecting pathogen is utilized to identify infected animals. In addition, it has been discovered that PCR analysis of manure samples can accurately identify infected animals and offspring for those species that consume placental remains after birth. Mink Aleutian Disease Virus (mADV) is one of several deadly DNA parvoviruses that can quickly reach epidemic proportions in a mink herd. PCR primers have been developed that generate amplicons to detect and identify the mADV. In addition, a previously unidentified strain of mADV has been discovered, genomically sequenced, and substantially detailed.

11 Claims, 21 Drawing Sheets

Specification includes a Sequence Listing.

FIGURE 3

```
ttaacgacgg gggaaggagt tgcctggctg ttccagcaaa agacctacac cgacaaagac      60
aacaaaccaa ccaaagcaac accaccactg aggacaacct cttctgatct aaggttagca     120
tttgaatcta ttgaagaaaa tttaaagtct tctactgaac acttaactaa caatgacata     180
aacttttgta aactaacctt ggggaaggcg ttggtggcac ttgataagca tgtaaggagc     240
cacagatggg atgctaacaa agttaacttt atctggcaaa tagaaaaagg atccactaag     300
caacttcata ttcactgttg cttaggttac tttgataaaa atgaagatcc taaggatgtt     360
caaaaatcct taggttggtt aattaaaaaa ataaataaag acttagcagt tatttatagt     420
aaccatcatt gtgacataca aaacattacg gatcctgaag ccaaagctaa taacttgaaa     480
gtgtggattg aagatgggcc tactaaacct tacaagtacc atcacaaaca aaccaaacag     540
gaatacaaca aagcagttca catgcaagac tataccataa tatatctgtt taacaaagat     600
aagataacta ctgatagtat ggatggttac tttgctgctg gtaacggtgg cattattgac     660
aacctaacta acaaggaacg aaaatgttta agaaaaatgt acttggatga gcagagttca     720
gatataatgg atgctgacat agactgggaa gatggccaag acgcgccaaa agtaactgac     780
caaactgact cagcaaccac aaaaacagga actagtttga tttggaaatc atgtgctacc     840
aaagtaacct caaaaaaaga ggttactgaa ccagttaagc aaccttctaa aaaactgtgc     900
tcagctcaaa gtactttaga tgctttattt gaccttggtt gctttactcc agaagatatg     960
attataaaat gcagtgacaa atatcttgaa ctatctttag aaccaaacgg acctcaaaaa    1020
attaacactt tacttcacat gaaccaagta aagacagcaa gcatgattag tgccttagat    1080
tgtattgtaa aatttaatga agaggaagat gatcaacctt taatagcaac cataaaagat    1140
atgggactta atgaacaaca ccttaagaaa gtactgtgta ccatactaac caagcaaggt    1200
ggaaaaagag gttgtatttg gttttatgga ccaggaggta ctggaaagac attgctagca    1260
tccttactat gtagagcaac agtaaacttt ggtgtggtta ctacaagcaa tccaaacttt    1320
ccatggactg actgtggcaa tagaaacatc atctgggctg aagaatgtgg taaccttggt    1380
aactgggttg aagactttaa agccattact ggaggtggtg atataaaagt agacaccaaa    1440
aacaagcaac ctcaatccat caaaggctgt gtgattgtaa caagcaacac caacattact    1500
aaagtaactg ttggatgtgt agaaacaaac gctcacgcag aaccactaaa acagagaatg    1560
gttaaaatac gttgcatgaa aaccatcaac cctacaacca aactaacacc gggaatgtta    1620
gcaaaatggc taagtacctg ggacagaata ccaatcaaac taaaccatga gatgcctgaa    1680
ctgtacttag gtaagtagcg tttggtaagt aacacatttt aaataccaac tttaaaacca    1740
acatcaattt atgaggttac tttactttac agagactact ggaccaaact cgagtgccac    1800
aactgccacg aagagtactg gcagcttaca acctactact gcaaggagtg cagaaagtgt    1860
gaacacggaa aactgcgata caccaaaaag gggtgcgagc agtgtgcctc cgaagcagca    1920
caagagacct cggcatgagt aaaagtaagt aacctactta aagtaaccta acaccatgac    1980
actttacttt gcttgtactt atgttacttt actttagttc ctcagcacta tcctgggaaa    2040
aagagaagtg ctccaagaca cgtgtttatt cagcaagcaa aaaagaagaa gcaaactaac    2100
cctgcggtgt accacggaga gaacaccata gaggaaatgg attctgctga acctgaacaa    2160
atggacactg agcaagcaac taaccaaact gctgaagctg gtggtggggg gggtgggggt    2220
ggtgggggtg gtggaggtgg tggggttggt aacagcactg gcggctttaa taacacaaca    2280
gaatttaaag taataaacaa tgaagtgtat attacttgtc acgctactag aatggtgcac    2340
atcaaccaag ctgacacaga tgaatactta atatttaatg ctggtagaac tactgatacc    2400
aaaacagctc aacagaaact aaacttagag ttttttgtat atgatgattt tcaccaacaa    2460
gtaatgacac cttggtttct ggtagatagc aacgcttggg gtgtatggat gagtcctaaa    2520
gactttcaac aaatgaaaac actatgtagt gaaattagtt tggttacttt ggaacaagaa    2580
atagacaatg taaccataaa aactgtaaca gaaaccaacc aaggtaacgc atcaaccaag    2640
caatttaaca atgacttgac tgcgtcgtta caagttgctt tagatactaa caacataatg    2700
ccatatactc cagctgcgcc gttgggggaa acactagggt ttgttccttg gagagcaacc    2760
aaaccaaccc aatataggta ttatcatcca tgttacattt acaacagata tcctaacatt    2820
caaaaaatgg gttcagaaca attagagtgg caaggaatac aagatgatta ccttagtgtg    2880
gatgaacagt actttaactt tattactata gagaacaaca tacctattaa cattctcaga    2940
acgggtgata actttcatac aggcttatat gagtttaaaa gtaaaccatg taaactaacc    3000
ttaagctacc agagtacacg ttgcttgggt ttacctcctc tttgcaaacc aaagacagat    3060
gcaacacaca aagtaacctc actagagaac ggagctgata tacaatacat acaaggagga    3120
```

FIGURE 3 CONTINUED

```
gataatataa gactgggtca cttttggggt gaggagagag gtaagaagaa cgcagaaatg      3180
aacagagtta gaccttacaa cataggttac caatatcctg aatggatcat accagcaggg      3240
ttacagggta gttactttgc tggaggacca agacaatgga gtgacacaac caaagggggg      3300
gagtcacaca gtcagcagtt acaacagaac tttagtacta gatacatcta tgacaggaac      3360
cacggtggag acaaccaggt agacttatta gatgcaatac ccattcatga aagaagtaac      3420
tactactcag accatgaact agagcaacat acagcaaagc aaccaaagtt acatacacca      3480
ccggttcacc actcaaagat agactcgtgg gaagaggaag gttggcctgc tgcttcaggc      3540
acacactttg aagatgaggt tatatactta gattacttta actttagtgg tgaacaggag      3600
atagagtttc cacatgaagt attagatgat ggtgcacaga tgaaaaagct acttaactca      3660
taccaaccaa cagttgcttt agacaacgtt ggtcctgtat acccatgggg acaagtatgg      3720
gataagaaac ctgatgtgga tcacaaacct agcatgaaca acagcgctcc atttgtatgt      3780
aaaaacaatc ctccaggtca actctttgtt aaactaacag aaaacctcac tgatacattt      3840
aactatgatg aagatccaga cagaataaaa acttatggtt actttacttg gagaggcaag      3900
cttgtactaa aaggtaaact aagccaagta acatgctgga atcctgtcaa gagagaactc      3960
ataggagaac ctggtgtatt tagtaaagac aactatcaca aacagatacc aaacaacaaa      4020
ggtaactttg aaatagggtt acaatatgga agaagcacta tcaaatatat ctactaaagt      4080
aacctatgta atatgttact atgttactat gatgatatct caataaaagt tacatgaaga      4140
gtgaacaac
```

FIGURE 4 (CONTINUED)

```
G-strain    1     ATTAATTCTC AACCAATATT CGTTAGCAAC CAACACCAGC TCGCTTCGCT
Stahl             .......... .......... .......... .......... ..........

G-strain    51    CGCGCACCTT CGGCGCTGGT GTTGGGCGCT TCGCGCTTGC TAACTTCATA
Stahl             .......... .......... .......... .......... ..........

G-strain    101   TTGGTTGAGA ATTAATCCGT GTCTTTCCTG TGGAATGAGG AAGTAGTGTG
Stahl             .......... .......... .......... .......... ..........

G-strain    151   GTATATAAGC AGAGGTTGCT TGGAGCAAAG CACAGACCGG TTACAGCAAA
Stahl             .......... .......... .......... .......... ..........

G-strain    201   GTAACATGGC TCAGGCTCAA ATTGATGAGC AGAGGAGACT GCAGGACCTG
Stahl             .......... .......... .......... .......... ..........

                                            V1a-F
G-strain    251   TATGTGCAGT TGAAGAAGGA GATTAACGAC GGTG.AAGGA GTTGCCTGGT
Stahl       1     .........T T......... ..TTAACGAC GGGGGAAGGA GTTGCCTGGC

G-strain    300   TGTTCCAACA AAAGACCTAC ACCGACAAGG ACAACAAACC AACCAAAGCA
Stahl       29    TGTTCCAGCA AAAGACCTAC ACCGACAAAG ACAACAAACC AACCAAAGCA

                                               V0-R1
G-strain    350   ACACCGCCAC TGAGGACAAC CTCTTCTGAC CTAAGGTTAG CTTTTGACTC
Stahl       79    ACACCACCAC TGAGGACAAC CTCTTCTGAT CTAAGGTTAG CATTTGAATC

G-strain    400   TATTGAAGAG AATTTAACAG CTTCTAATGA ACACTTAACT AACAATGAGA
Stahl       129   TATTGAAGAA AATTTAAAGT CTTCTACTGA ACACTTAACT AACAATGACA

G-strain    450   TAAACTTTTG TAAACTAACC TTGGGGAAGA CGTTGCTGTT AATTGATAAG
Stahl       179   TAAACTTTTG TAAACTAACC TTGGGGAAGG CGTTGGTGGC ACTTGATAAG

G-strain    500   CATGTAAAAA GCCACAGATG GGATAGTAAC AAAGTTAACT TAATTTGGCA
Stahl       229   CATGTAAGGA GCCACAGATG GGATGCTAAC AAAGTTAACT TTATCTGGCA

G-strain    550   AATAGAAAAA GGAAAAACTC AGCAATTTCA TATTCACTGT TGCTTAGGTT
Stahl       279   AATAGAAAAA GGATCCACTA AGCAACTTCA TATTCACTGT TGCTTAGGTT

G-strain    600   ACTTTGATAA GAATGAAGAT CCTAAGGATG TTCAAAAATC CTTAGGTTGG
Stahl       329   ACTTTGATAA AAATGAAGAT CCTAAGGATG TTCAAAAATC CTTAGGTTGG

G-strain    650   TTTATGAAAA GACTAAATAA AGACCTAGCA GTTATCTATA GTAACCATCA
Stahl       379   TTAATTAAAA AAATAAATAA AGACTTAGCA GTTATTTATA GTAACCATCA
```

FIGURE 4 (CONTINUED)

| | | |
|---|---|---|
| G-strain | 700 | TTGTGACATA CAAGATATTA AGGATCCTGA AGATAGAGCT AAGAACCTAA |
| Stahl | 429 | TTGTGACATA CAAAACATTA CGGATCCTGA AGCCAAAGCT AATAACTTGA |
| G-strain | 750 | AAGTGTGGAT TGAAGATGGA CCTACTAAGC CTTACAAATA TTTTAACAAA |
| Stahl | 479 | AAGTGTGGAT TGAAGATGGG CCTACTAAAC CTTACAAGTA CCATCACAAA |
| G-strain | 800 | CAAACCAAAC AAGACTACAA TAAACCAGTT CACTTGAGAG ACTATACATT |
| Stahl | 529 | CAAACCAAAC AGGAATACAA CAAAGCAGTT CACATGCAAG ACTATACCAT |
| | | **V2-F** |
| G-strain | 850 | CATATACCTG TTTAACAAAG ATAAGATAAA TACAGATAGT ATGGA**TGGTT** |
| Stahl | 579 | AATATATCTG TTTAACAAAG ATAAGATAAC TACTGATAGT ATGGATGGTT |
| | | **V1-R** |
| G-strain | 900 | **ACTTTGCTGC TGGTAACGGT GGCATTGTTG ACA**ACCTAAC TAACAAAGAA |
| Stahl | 629 | ACTTTGCTGC TGGTAACGGT GGCATTATTG ACAACCTAAC TAACAAGGAA |
| G-strain | 950 | CGAAAAACTT TAAGAAAAAT GTACTTAGAT GAGCAGAGTT CAGATATAAT |
| Stahl | 679 | CGAAAATGTT TAAGAAAAAT GTACTTGGAT GAGCAGAGTT CAGATATAAT |
| G-strain | 1000 | GGATGCTAAT ATAGACTGGG AAGATGGCCA AGACGCGCCA AAAGTAACTG |
| Stahl | 729 | GGATGCTGAC ATAGACTGGG AAGATGGCCA AGACGCGCCA AAAGTAACTG |
| G-strain | 1050 | ACCAAACTGA CTCAGCAACC ACAAAAACAG GAACTAGTTT GATTTGGAAA |
| Stahl | 779 | ACCAAACTGA CTCAGCAACC ACAAAAACAG GAACTAGTTT GATTTGGAAA |
| G-strain | 1100 | TCATGTGCTA CTAAAGTAAC CTCAAAAAAA GAAGTTGCTA ATCCAGTTCA |
| Stahl | 829 | TCATGTGCTA CCAAAGTAAC CTCAAAAAAA GAGGTTACTG AACCAGTTAA |
| G-strain | 1150 | GCAACCTTCT AAAAAACTGT ACTCAGCTCA AAGTACTTTA GATGCATTGT |
| Stahl | 879 | GCAACCTTCT AAAAAACTGT GCTCAGCTCA AAGTACTTTA GATGCTTTAT |
| | | **V1a-R** |
| G-strain | 1200 | **TTAACGTTGG TTGCTTTACT CCAGAAGA**TA TGATTATAAA GCAAAGTGAC |
| Stahl | 929 | TTGACCTTGG TTGCTTTACT CCAGAAGATA TGATTATAAA ATGCAGTGAC |
| G-strain | 1250 | AAATACCTTG AACTATCTTT AGAACCAAAC GGGCCTCAAA AAATTAACAC |
| Stahl | 979 | AAATATCTTG AACTATCTTT AGAACCAAAC GGACCTCAAA AAATTAACAC |
| G-strain | 1300 | TTTACTTCAC ATGAACCAAG TAAAGACATC AACCATGATT ACTGCTTTTG |
| Stahl | 1029 | TTTACTTCAC ATGAACCAAG TAAAGACAGC AAGCATGATT AGTGCCTTAG |

FIGURE 4 (CONTINUED)

```
G-strain     1350     ATTGTATTAT AAAATTTAAT GAAGAGGAAG ATGACAAACC TTTGCTAGCA
Stahl        1079     ATTGTATTGT AAAATTTAAT GAAGAGGAAG ATGATCAACC TTTAATAGCA

G-strain     1400     ACTATAAAAG ACATGGGACT TAATGAACAA TACCTTAAGA AGGTACTATG
Stahl        1129     ACCATAAAAG ATATGGGACT TAATGAACAA CACCTTAAGA AAGTACTGTG

                        V3-F
G-strain     1450     TACCATCCTA ACCAAGCAAG GTGGAAAGAG AGGTTGTATT TGGTTCTATG
Stahl        1179     TACCATACTA ACCAAGCAAG GTGGAAAAAG AGGTTGTATT TGGTTTTATG

G-strain     1500     GACCGGGGGG CACTGGAAAA ACCTTGCTAG CATCTTTAAT ATGTAAAGCA
Stahl        1229     GACCAGGAGG TACTGGAAAG ACATTGCTAG CATCCTTACT ATGTAGAGCA

G-strain     1550     ACAGTAAACT ATGGTATGGT TACTACAAGC AATCCAAACT TTCCATGGAC
Stahl        1279     ACAGTAAACT TTGGTGTGGT TACTACAAGC AATCCAAACT TTCCATGGAC

G-strain     1600     TGACTGTGGC AATAGAAACA TCATTTGGGC TGAAGAGTGT GGTAACTTTG
Stahl        1329     TGACTGTGGC AATAGAAACA TCATCTGGGC TGAAGAATGT GGTAACCTTG

G-strain     1650     GTAACTGGGT TGAAGACTTT AAAGCCATTA CTGGAGGTGG TGATGTAAAA
Stahl        1379     GTAACTGGGT TGAAGACTTT AAAGCCATTA CTGGAGGTGG TGATATAAAA

G-strain     1700     GTAGACACCA AGAACAAGCA ACCTCAATCT ATTAAAGGCT GTGTGATTGT
Stahl        1429     GTAGACACCA AAAACAAGCA ACCTCAATCC ATCAAAGGCT GTGTGATTGT

G-strain     1750     AACAAGCAAC ACCAACATAA CCAAAGTAAC TGTTGGATGT GTGGAAACAA
Stahl        1479     AACAAGCAAC ACCAACATTA CTAAAGTAAC TGTTGGATGT GTAGAAACAA

                                                   V2-R
G-strain     1800     ACGCTCACGC AGAGCCACTT AAACAGAGGA TGATTAAGAT ACGTTGCATG
Stahl        1529     ACGCTCACGC AGAACCACTA AAACAGAGAA TGGTTAAAAT ACGTTGCATG

G-strain     1850     AAAACCATCA ACCCTAAAAC TAAAATAACA CCAGGCATGT TAAAAAGATG
Stahl        1579     AAAACCATCA ACCCTACAAC CAAACTAACA CCGGGAATGT TAGCAAAATG

G-strain     1900     GCTAAATACC TGGGATAGAC AACCAATTCA ACTAAGCCAT GAGATGCCTG
Stahl        1629     GCTAAGTACC TGGGACAGAA TACCAATCAA ACTAAACCAT GAGATGCCTG

G-strain     1950     AACTGTACTT AGGTAAGTGC CGTT.GGTAA GTAACACATT TTAAATGCCA
Stahl        1679     AACTGTACTT AGGTAAGTAG CGTTTGGTAA GTAACACATT TTAAATACCA

G-strain     1999     ACTTTAAA.C CAACATCAAT TTATGAGGTT ACTTTACTTT ACAGAGACTA
```

FIGURE 4 (CONTINUED)

```
Stahl     1729   ACTTTAAAAC CAACATCAAT TTATGAGGTT ACTTTACTTT ACAGAGACTA

                                   V4-F
G-strain  2048   CTGGACCAAA CTCGAGTGCC ACAACTGCCA CGAAGAATAC TGGCAACTCA
Stahl     1779   CTGGACCAAA CTCGAGTGCC ACAACTGCCA CGAAGAGTAC TGGCAGCTTA

G-strain  2098   CAACCTACTA CTGCAAAGAG TGCAGAAAGT GTGAACACGG AAAACTGCGA
Stahl     1829   CAACCTACTA CTGCAAGGAG TGCAGAAAGT GTGAACACGG AAAACTGCGA

G-strain  2148   CACACCAAAA AGGAGTGCGA GCAGTGTGCC TGCAAAGCAG CACAAGAGAC
Stahl     1879   TACACCAAAA AGGGGTGCGA GCAGTGTGCC TCCGAAGCAG CACAAGAGAC

G-strain  2198   CTCGGCATGA GTAAAAGTAA ATAACCTACT TAAAGTAACC TAACACCATA
Stahl     1929   CTCGGCATGA GTAAAAGTAA GTAACCTACT TAAAGTAACC TAACACCATG

G-strain  2248   ACACTTTACT TTCCTTGTAC TTATGTTACT TTACTTTAGT TCCTCAGCAC
Stahl     1979   ACACTTTACT TTGCTTGTAC TTATGTTACT TTACTTTAGT TCCTCAGCAC

                                                  V3-R
G-strain  2298   TATCCTGGGA AAAAGAGAAG TGCTCCAAGA CACGTGTTTA TTCAGCAAGC
Stahl     2029   TATCCTGGGA AAAAGAGAAG TGCTCCAAGA CACGTGTTTA TTCAGCAAGC

                       V4a-F
G-strain  2348   AAAAAAAGAAG AAGCAAACTA ACCCTGCGGT CTACCACGGA GAGGACACCA
Stahl     2079   AAAAAAAGAAG AAGCAAACTA ACCCTGCGGT GTACCACGGA GAGAACACCA

G-strain  2398   TAGAGGAAAT GGATTCTACT GAAGCTGAAC AAATGGACAC TGAGCAAGCA
Stahl     2129   TAGAGGAAAT GGATTCTGCT GAACCTGAAC AAATGGACAC TGAGCAAGCA

G-strain  2448   ACTAACCAAA CTGCTGAAGC TGGTGGTGGG GGGGGTGGGG GTGGTGGGGG
Stahl     2179   ACTAACCAAA CTGCTGAAGC TGGTGGTGGG GGGGGTGGGG GTGGTGGGGG

                                                V4b-F
G-strain  2498   TGGTGGTGGT GGTGGTGGGG TTGGTAACAG CACTGGCGGC TTTAATAACA
Stahl     2229   TGGTGGAGGT GGTGG...GG TTGGTAACAG CACTGGCGGC TTTAATAACA

G-strain  2548   CAACAGAATT CAAAGTAATA AACAATGAAG TGTATATTAC TTGTCACGCT
Stahl     2276   CAACAGAATT TAAAGTAATA AACAATGAAG TGTATATTAC TTGTCACGCT

G-strain  2598   ACTAGAATGG TACACATTAA CCAAGCTGAC ACAGACGAAT ACTTGATATT
Stahl     2326   ACTAGAATGG TGCACATCAA CCAAGCTGAC ACAGATGAAT ACTTAATATT

G-strain  2648   TAATGCTGGT AGAACTACTG ATACCAAAAC ACATCAGCAA AAACTAAACT
Stahl     2376   TAATGCTGGT AGAACTACTG ATACCAAAAC AGCTCAACAG AAACTAAACT
```

FIGURE 4 (CONTINUED)

```
G-strain     2698    TAGAATTTTT TGTATATGAT GATTTTCACC AACAAGTAAT GACACCTTGG
Stahl        2426    TAGAGTTTTT TGTATATGAT GATTTTCACC AACAAGTAAT GACACCTTGG

G-strain     2748    TATATAGTAG ATAGCAACGC TTGGGGTGTA TGGATGAGTC CTAAAGACTT
Stahl        2476    TTTCTGGTAG ATAGCAACGC TTGGGGTGTA TGGATGAGTC CTAAAGACTT

G-strain     2798    TCAACAAATG AAAACACTGT GTAGTGAAAT TAGTTTGGTT ACTTTGGAAC
Stahl        2526    TCAACAAATG AAAACACTAT GTAGTGAAAT TAGTTTGGTT ACTTTGGAAC

G-strain     2848    AAGAAATAGA CAATGTAACC ATAAAAACTG TAACAGAAAC CAACCAAGGT
Stahl        2576    AAGAAATAGA CAATGTAACC ATAAAAACTG TAACAGAAAC CAACCAAGGT

G-strain     2898    AACGCATCTA CCAAGCAATT CAACAATGAC TTAACTGCGT CGTTACAGGT
Stahl        2626    AACGCATCAA CCAAGCAATT TAACAATGAC TTGACTGCGT CGTTACAAGT

G-strain     2948    TGCTTTAGAT ACTAACAACA TACTGCCATA TACTCCAGCT GCGCCGTTGG
Stahl        2676    TGCTTTAGAT ACTAACAACA TAATGCCATA TACTCCAGCT GCGCCGTTGG

                                                 V5-F                 V4-R
G-strain     2998    GGGAAACACT GGGCTTTGTT CCTTGGAGAG CAACCAAACC AACCCAATAT
Stahl        2726    GGGAAACACT AGGGTTTGTT CCTTGGAGAG CAACCAAACC AACCCAATAT

G-strain     3048    AGGTATTATC ATCCATGTTA CATTTACAAC AGATATCCTA ACATTCAAAA
Stahl        2776    AGGTATTATC ATCCATGTTA CATTTACAAC AGATATCCTA ACATTCAAAA

                    H Y P E R V A R I A B L E   R E G I O N
G-strain     3098    AGTTGCAACA GAAACACTAA CCTGGGATGC AGTACAAGAT GATTACCTTA
Stahl        2826    AATGGGTTCA GAACAATTAG AGTGGCAAGG AATACAAGAT GATTACCTTA

G-strain     3148    GTGTGGATGA ACAGTACTTT AACTTTATTA CTATAGAGAA CAACATACCT
Stahl        2876    GTGTGGATGA ACAGTACTTT AACTTTATTA CTATAGAGAA CAACATACCT

G-strain     3198    ATTAACATTC TCAGAACGGG AGATAACTTT CATACAGGCT TGTATGAGTT
Stahl        2926    ATTAACATTC TCAGAACGGG TGATAACTTT CATACAGGCT TATATGAGTT

G-strain     3248    TAACAGTAAA CCATGTAAAC TAACCTTAAG CTATCAAAGT ACACGTTGCT
Stahl        2976    TAAAAGTAAA CCATGTAAAC TAACCTTAAG CTACCAGAGT ACACGTTGCT

                                           V5a-R
G-strain     3298    TGGGGCTACC TCCTCTCTGC AAACCAAAGA CAGATACAAC ACACAAAGTA
Stahl        3026    TGGGTTTACC TCCTCTTTGC AAACCAAAGA CAGATGCAAC ACACAAAGTA
```

FIGURE 4 (CONTINUED)

```
G-strain    3348    ACCTCAAAAG AAAACGGAGC TGACCTAATT TACATACAAG GACAAGATAA
Stahl       3076    ACCTCACTAG AGAACGGAGC TGATATACAA TACATACAAG GAGGAGATAA

G-strain    3398    TACCAGACTA GGTCACTTTT GGGGTGAGGA AAGAGGTAAG AAAAACGCAG
Stahl       3126    TATAAGACTG GGTCACTTTT GGGGTGAGGA GAGAGGTAAG AAGAACGCAG

G-strain    3448    AGATGAACAG AATTAGACCT TACAACATAG GTTACCAATA TCCTGAATGG
Stahl       3176    AAATGAACAG AGTTAGACCT TACAACATAG GTTACCAATA TCCTGAATGG

                                          V5b-R
G-strain    3498    ATAATACCAG CAGGGTTACA GGGTAGTTAC TTTGCTGGAG GACCAAGACA
Stahl       3226    ATCATACCAG CAGGGTTACA GGGTAGTTAC TTTGCTGGAG GACCAAGACA

                               V6a-F
G-strain    3548    GTGGAGTGAC ACAACCAAAG GTGCAGGTAC ACACAGTCAA CACTTACAAC
Stahl       3276    ATGGAGTGAC ACAACCAAAG GGGGGGAGTC ACACAGTCAG CAGTTACAAC

G-strain    3598    AGAACTTTAG TACTAGGTAC ATCTATGACA GAAACCACGG TGGAGACAAC
Stahl       3326    AGAACTTTAG TACTAGATAC ATCTATGACA GGAACCACGG TGGAGACAAC

G-strain    3648    GAGGTAGACC TATTAGATGG AATACCCATT CATGAAAGAA GTAACTACTA
Stahl       3376    CAGGTAGACT TATTAGATGC AATACCCATT CATGAAAGAA GTAACTACTA

                                                                   V6-F
G-strain    3698    CTCAGACAAT GAGATAGAGC AACATACAGC AAAGCAACCA AAGTTACGTA
Stahl       3426    CTCAGACCAT GAACTAGAGC AACATACAGC AAAGCAACCA AAGTTACATA

G-strain    3748    CACCACCCAT TCACCACTCA AAAATAGACT CGTGGGAAGA AGAAGGTTGG
Stahl       3476    CACCACCGGT TCACCACTCA AAGATAGACT CGTGGGAAGA GGAAGGTTGG

                                             V5-R
G-strain    3798    CCTGCTGCTT CAGGCACACA CTTTGAAGAT GAGGTTATAT ACCTAGACTA
Stahl       3526    CCTGCTGCTT CAGGCACACA CTTTGAAGAT GAGGTTATAT ACTTAGATTA

G-strain    3848    CTTTAACTTT AGTGGTGAAC AGGAGCTAAA CTTTCCACAT GAAGTATTAG
Stahl       3576    CTTTAACTTT AGTGGTGAAC AGGAGATAGA GTTTCCACAT GAAGTATTAG

G-strain    3898    ATGATGCTGC TCAGATGAAA AAGCTACTTA ACTCATACCA ACCAACAGTT
Stahl       3626    ATGATGGTGC ACAGATGAAA AAGCTACTTA ACTCATACCA ACCAACAGTT

G-strain    3948    GCTCAAGACA ACGTTGGTCC TGTATACCCG TGGGGACAGA TATGGGACAA
Stahl       3676    GCTTTAGACA ACGTTGGTCC TGTATACCCA TGGGGACAAG TATGGGATAA

G-strain    3998    GAAACCTCAT ATGGATCACA AACCTAGCAT GAACAACAAC GCTCCATTTG
Stahl       3726    GAAACCTGAT GTGGATCACA AACCTAGCAT GAACAACAGC GCTCCATTTG
```

FIGURE 4 (CONTINUED)

```
G-strain    4048   TATGTAAAAA CAACCCTCCA GGTCAACTCT TTGTTAAACT AACAGAAAAC
Stahl       3776   TATGTAAAAA CAATCCTCCA GGTCAACTCT TTGTTAAACT AACAGAAAAC

G-strain    4098   CTCACTGATA CATTTAACTA TGATGAAAAT CCAGACAGAA TAAAAACCTA
Stahl       3826   CTCACTGATA CATTTAACTA TGATGAAGAT CCAGACAGAA TAAAAACTTA

G-strain    4148   TGGTTACTTT ACTTGGAGAG GCAAGCTTGT ACTAAAAGGC AAACTAAGCC
Stahl       3876   TGGTTACTTT ACTTGGAGAG GCAAGCTTGT ACTAAAAGGT AAACTAAGCC

                                              V7-F2
G-strain    4198   AAGTAACATG CTGGAATCCT GTTAAGAGAG AACTCATAGG AGAACCTGGT
Stahl       3926   AAGTAACATG CTGGAATCCT GTCAAGAGAG AACTCATAGG AGAACCTGGT

G-strain    4248   GTATTTACTA AAGACAAGTA TCACAAACAG ATACCAAACA ACAAAGGTAA
Stahl       3976   GTATTTAGTA AAGACAACTA TCACAAACAG ATACCAAACA ACAAAGGTAA

G-strain    4298   CTTTGAAATA GGGTTACAAT ATGGAAGAAG TACTATCAAA TATATCTACT
Stahl       4026   CTTTGAAATA GGGTTACAAT ATGGAAGAAG CACTATCAAA TATATCTACT

G-strain    4348   AAAGTAACCT GTGTACTATG TTACTATGTT ACTATGATAA TATCTCAATA
Stahl       4076   AAAGTAACCT ATGTAATATG TTACTATGTT ACTATGATGA TATCTCAATA

                                                         V6a-R
G-strain    4398   AAAGTTACAT GAATAGTGAA CAACCTAAAT ACTGTGTACT TCCTTATTTT
Stahl       4126   AAAGTTACAT GAAGAGTGAA CAAC...... .......... ..........

G-strain    4448   ACCAGAAAGT GGCGGATTAA AATAAACCTA CATTCTATAC TATCTATATA
Stahl              .......... .......... .......... .......... ..........

G-strain    4498   CTACTAACTA ACCTATAGGT TACTTTGCTT TGATATACTG ATGTAGGAAT
Stahl              .......... ...TATGGG. .......... .......... .....GG...

G-strain    4548   ACAGGATACT AACATTTATA TATATACTAA CATCTATACT ACTAACCTAA
Stahl              .......... .......... .......... .......... ..........

G-strain    4598   CTATGGCCTA ATGTATGCAG TGTCGGCGTC GCCGACAACT ACATTATATT
Stahl              .......... .......... ....GGGGTC CCC....... ..........

G-strain    4648   ATTAGGCATA GTTAGGTTAG TAGTATAGAT GTTAGTATAT ATATAAATGT
Stahl              .......... .......... .......... .......... ..........
```

FIGURE 4 (CONTINUED)

```
G-strain     4698   TAGTATCCTG TGTTCCTACT TCAGTATATA AAGAAAGTTT CCTATAGGTG
Stahl               .......... .......... .........A AAAAA..... ..........

                                 V6-R
G-strain     4748   GGTTTGCGGT CTATCTAGAG TTGTGGTCCG TATTGGTTTC TGTAAAGGAC
Stahl               .......... .......... .......... .......... ..........

G-strain     4798   CTGA
Stahl               ....
```

FIGURE 5A

```
       LTTGEGVAWL FQQKTYTDKD NKPTKATPPL RTTSSDLRLA FESIEENLKS STEHLTNNDI
60     NFCKLTLGKA LVALDKHVRS HRWDANKVNF IWQIEKGSTK QLHIHCCLGY FDKNEDPKDV
120    QKSLGWLIKK INKDLAVIYS NHHCDIQNIT DPEAKANNLK VWIEDGPTKP YKYHHKQTKQ
180    EYNKAVHMQD YTIIYLFNKD KITTDSMDGY FAAGNGGIID NLTNKERKCL RKMYLDEQSS
240    DIMDADIDWE DGQDAPKVTD QTDSATTKTG TSLIWKSCAT KVTSKKEVTE PVKQPSKKLC
300    SAQSTLDALF DLGCFTPEDM IIKCSDKYLE LSLEPNGPQK INTLLHMNQV KTASMISALD
360    CIVKFNEEED DQPLIATIKD MGLNEQHLKK VLCTILTKQG GKRGCIWFYG PGGTGKTLLA
420    SLLCRATVNF GVVTTSNPNF PWTDCGNRNI IWAEECGNLG NWVEDFKAIT GGGDIKVDTK
480    NKQPQSIKGC VIVTSNTNIT KVTVGCVETN AHAEPLKQRM VKIRCMKTIN PTTKLTPGML
540    AKWLSTWDRI PIKLNHEMPE LYLGK
```

FIGURE 5B

```
       HHDTLLCLYL CYFTLVPQHY PGKKRSAPRH VFIQQAKKKK QTNPAVYHGE NTIEEMDSAE
60     PEQMDTEQAT NQTAEAGGGG GGGGGGGGGG GVGNSTGGFN NTTEFKVINN EVYITCHATR
120    MVHINQADTD EYLIFNAGRT TDTKTAQQKL NLEFFVYDDF HQQVMTPWFL VDSNAWGVWM
180    SPKDFQQMKT LCSEISLVTL EQEIDNVTIK TVTETNQGNA STKQFNNDLT ASLQVALDTN
240    NIMPYTPAAP LGETLGFVPW RATKPTQYRY YHPCYIYNRY PNIQKMGSEQ LEWQGIQDDY
300    LSVDEQYFNF ITIENNIPIN ILRTGDNFHT GLYEFKSKPC KLTLSYQSTR CLGLPPLCKP
360    KTDATHKVTS LENGADIQYI QGGDNIRLGH FWGEERGKKN AEMNRVRPYN IGYQYPEWII
420    PAGLQGSYFA GGPRQWSDTT KGGESHSQQL QQNFSTRYIY DRNHGGDNQV DLLDAIPIHE
480    RSNYYSDHEL EQHTAKQPKL HTPPVHHSKI DSWEEEGWPA ASGTHFEDEV IYLDYFNFSG
540    EQEIEFPHEV LDDGAQMKKL LNSYQPTVAL DNVGPVYPWG QVWDKKPDVD HKPSMNNSAP
600    FVCKNNPPGQ LFVKLTENLT DTFNYDEDPD RIKTYGYFTW RGKLVLKGKL SQVTCWNPVK
660    RELIGEPGVF SKDNYHKQIP NNKGNFEIGL QYGRSTIKYI Y
```

FIGURE 6

```
                    130       140       150       160       170       180
                      |         |         |         |         |         |
NC_001662    RMVHINQADTDEYLIFNAGRTTDTKTHQQKLNLEFFVYDDFHQQVMTPWYIVDSNAWGVW
M20036       RMVHINQADTDEYLIFNAGRTTDTKTHQQKLNLEFFVYDDFHQQVMTPWYIVDSNAWGVW
G_strain     RMVHINQADTDEYLIFNAGRTTDTKTHQQKLNLEFFVYDDFHQQVMTPWYIVDSNAWGVW
AF124791     RMVHINQADTDEYLIFNAGRTTDTKTHQQKLNLEFFVYDDFHQQVMTPWYLVDSNAWGVW
X97629       RMVHINQADTDEYLIFNAGRTTDTKTHQQKLNLEFFVYDDFHQQVMTPWYIVDSNAWGVW
Utah1x2      RMVHINQADTDEYLIFNADRTTDTKTAQKKLNLEFFVYDDFHQQVMTPWFIVDSNAWGVW
Z18276       RMVHINQADTDEYLIFNAGRTTDTKTAQKKLNLEFFVYDDFHQQVMTPWFIVDSNAWGVW
Stahlx1      RMVHINQADTDEYLIFNAGRTTDTKTAQQKLNLEFFVYDDFHQQVMTPWFLVDSNAWGVW
Pullman      RMVHINQADTDEYLIFNAGRTTDTKTAQPKLNLEFFVYDDFHQQVMTPWFMVDSNAWGVW
             ******************.******* * ********************::*********
Prim.cons.   RMVHINQADTDEYLIFNAGRTTDTKTHQQKLNLEFFVYDDFHQQVMTPWYIVDSNAWGVW

                    190       200       210       220       230       240
                      |         |         |         |         |         |
NC_001662    MSPKDFQQMKTLCSEISLVTLEQEIDNVTIKTVTETNQGNASTKQFNNDLTASLQVALDT
M20036       MSPKDFQQMKTLCSEISLVTLEQEIDNVTIKTVTETNQGNASTKQFNNDLTASLQVALDT
G_strain     MSPKDFQQMKTLCSEISLVTLEQEIDNVTIKTVTETNQGNASTKQFNNDLTASLQVALDT
AF124791     MSPKDFQQMKTLCSEISLLSLEQEIDNVTIKTVTETNQGNASTKQFNNDLTASLQVALDT
X97629       MSPKDFQQMKTLCSEISLVTLEQEIDNVTIKTVTETNQGNASTKQFNNDLTASLQVALDT
Utah1x2      MSPKDFQQMKTLCSEISLVTLEQEIDNVTIKTVTETNQGNASTKQFNNDLTASLQVALDT
Z18276       MSPKDFQQMKTLCSEISLVTLEQEIDNVTIKTVTETNQGNASTKQFNNDLTASLQVALDT
Stahlx1      MSPKDFQQMKTLCSEISLVTLEQEIDNVTIKTVTETNQGNASTKQFNNDLTASLQVALDT
Pullman      MSPKDFQQMKTLCSEISLVTLEQEIDNVTIKTVTETNQGNATVKQYNNDLTASLQVALDT
             ******************::*********************:.**:**************
Prim.cons.   MSPKDFQQMKTLCSEISLVTLEQEIDNVTIKTVTETNQGNASTKQFNNDLTASLQVALDT

                    250       260       270       280       290       300
                      |         |         |         |         |         |
NC_001662    NNILPYTPAAPLGETLGFVPWRATKPTQYRYYHPCYIYNRYPNIQKVATETLTWDAVQDD
M20036       NNILPYTPAAPLGETLGFVPWRATKPTQYRYYHPCYIYNRYPNIQKVATETLTWDAVQDD
G_strain     NNILPYTPAAPLGETLGFVPWRATKPTQYRYYHPCYIYNRYPNIQKVATETLTWDAVQDD
AF124791     NNILPYTPAAPLGETLGFVPWRATKPTQYRYYHPCYIYNRYPNIQKVAGETLTWDAVQDD
X97629       NNILPYTPAAPLGETLGFVPWRATKPTQYRYYHPCYIYNRYPNIQKVATETLTWDAVQDD
Utah1x2      NNILPYTPAAPLGETLGFVPWRATKPTQYRYYHPCYIYNRYPNIQKLGQEQLEWTGTQDD
Z18276       NNILPYTPAAPLGETLGFVPWRATKPTQYRYYHPCYIYNRYPNIQKMGQEQLEWTGTQDD
Stahlx1      NNIMPYTPAAPLGETLGFVPWRATKPTQYRYYHPCYIYNRYPNIQKMGSEQLEWQGIQDD
Pullman      NNILPYTPAAPLGETLGFVPWRATKPTQYRYYHPCYIYNRYPNIQKAAQSPLEWTGTQDD
             ***:****************************************** . . * * . ***
Prim.cons.   NNILPYTPAAPLGETLGFVPWRATKPTQYRYYHPCYIYNRYPNIQKVATETLTWDAVQDD

                    310       320       330       340       350       360
                      |         |         |         |         |         |
NC_001662    YLSVDEQYFNFITIENNIPINILRTGDNFHTGLYEFNSKPCKLTLSYQSTRCLGLPPLCK
M20036       YLSVDEQYFNFITIENNIPINILRTGDNFHTGLYEFNSKPCKLTLSYQSTRCLGLPPLCK
G_strain     YLSVDEQYFNFITIENNIPINILRTGDNFHTGLYEFNSKPCKLTLSYQSTRCLGLPPLCK
AF124791     YLSVDEQYFNFITIENNIPINILRTGDNFHTGLYEFNSKPCKLTLSYQSTRCLGLPPLCK
X97629       YLSVDEQYFNFITIENNIPINILRTGDNFHTGLYEFNSKPCKLTLSYQSTRCLGLPPLCK
Utah1x2      YLSVDEQYFNFITIENNIPINILRTGDNFHTGLYEFNSKPCKLTLSYQSTRCLGLPPLCK
Z18276       YLSVDEQYFNFITIENNIPINILRTGDNFHTGLYEFNSKPCKLTLSYQSTRCLGLPPLCK
Stahlx1      YLSVDEQYFNFITIENNIPINILRTGDNFHTGLYEFKSKPCKLTLSYQSTRCLGLPPLCK
Pullman      YLSVDEQYFNFITIENNIPINILRTGDNFHSGIYEFKSKPCKLTLSYQSTRCLGLPPLCK
             ******************************:*:***:***********************
Prim.cons.   YLSVDEQYFNFITIENNIPINILRTGDNFHTGLYEFNSKPCKLTLSYQSTRCLGLPPLCK
```

Placental PCR

Follow-up PCR

SEQUENCE LISTING

```
<160> NUMBER OF SEQ ID NOS: 32

<210> SEQ ID NO 1
```

-continued

<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1
ttaacgacgg tgaaggagtt gcct 24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 2
tcttctggag taaagcaacc aacg 24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 3
tggttacttt gctgctggta acgg 24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 4
tcctctgttt aagtggctct gcgt 24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5
accatcctaa ccaagcaagg tgga 24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 6
acacgtgtct tggagcactt ctct 24

<210> SEQ ID NO 7
<211> LENGTH: 24

<212> TYPE: DNA
<213> ORGANISM: Artificial Sequence
<220> FEATURE:
<223> OTHER INFORMATION: Description of Artificial Sequence: Synthetic
primer

<400> SEQUENCE: 7
tgccacaact gccacgaaga atac 24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
attgggttgg tttggttgct ctcc 24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
cagcactggc ggctttaata acac 24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
actaccctgt aaccctgctg gtat 24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11
ggagagcaac caaaccaacc caat 24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 12
ttcaaagtgt gtgcctgaag cagc 24

<210> SEQ ID NO 13
<211> LENGTH: 24
<212> TYPE: DNA

<213> ORGANISM: Artificial Sequence
<220> FEATURE:
<223> OTHER INFORMATION: Description of Artificial Sequence: Synthetic
primer

<400> SEQUENCE: 13
caaccaaagg tgcaggtaca caca 24

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
ggaagtacac agtatttagg ttgttcac 28

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15
aacatcatcc ctgcttccac tggt 24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16
tgttgaagtc gcaggagaca acct 24

<210> SEQ ID NO 17
<211> LENGTH: 4149
<212> TYPE: DNA
<213> ORGANISM: Aleutian mink disease virus

<400> SEQUENCE: 17
ttaacgacgg gggaaggagt tgcctggctg ttccagcaaa agacctacac cgacaaagac 60
aacaaaccaa ccaaagcaac accaccactg aggacaacct cttctgatct aaggttagca 120
tttgaatcta ttgaagaaaa tttaaagtct tctactgaac acttaactaa caatgacata 180
aacttttgta aactaacctt ggggaaggcg ttggtggcac ttgataagca tgtaaggagc 240
cacagatggg atgctaacaa agttaacttt atctggcaaa tagaaaaagg atccactaag 300
caacttcata ttcactgttg cttaggttac tttgataaaa atgaagatcc taaggatgtt 360
caaaaatcct taggttggtt aattaaaaaa ataaataaag acttagcagt tatttatagt 420
aaccatcatt gtgacataca aaacattacg gatcctgaag ccaaagctaa taacttgaaa 480
gtgtggattg aagatgggcc tactaaacct tacaagtacc atcacaaaca aaccaaacag 540
gaatacaaca aagcagttca catgcaagac tataccataa tatatctgtt taacaaagat 600
aagataacta ctgatagtat ggatggttac tttgctgctg gtaacggtgg cattattgac 660
aacctaacta acaaggaacg aaaatgttta agaaaaatgt acttggatga gcagagttca 720

-continued

```
gatataatgg atgctgacat agactgggaa gatggccaag acgcgccaaa agtaactgac    780
caaactgact cagcaaccac aaaaacagga actagtttga tttggaaatc atgtgctacc    840
aaagtaacct caaaaaaaga ggttactgaa ccagttaagc aaccttctaa aaaactgtgc    900
tcagctcaaa gtactttaga tgctttattt gaccttggtt gctttactcc agaagatatg    960
attataaaat gcagtgacaa atatcttgaa ctatctttag aaccaaacgg acctcaaaaa   1020
attaacactt tacttcacat gaaccaagta aagacagcaa gcatgattag tgccttagat   1080
tgtattgtaa aatttaatga agaggaagat gatcaacctt taatagcaac cataaaagat   1140
atgggactta atgaacaaca ccttaagaaa gtactgtgta ccatactaac caagcaaggt   1200
ggaaaaagag gttgtatttg gttttatgga ccaggaggta ctggaaagac attgctagca   1260
tccttactat gtagagcaac agtaaacttt ggtgtggtta ctacaagcaa tccaaacttt   1320
ccatggactg actgtggcaa tagaaacatc atctgggctg aagaatgtgg taaccttggt   1380
aactgggttg aagactttaa agccattact ggaggtggtg atataaaagt agacaccaaa   1440
aacaagcaac ctcaatccat caaaggctgt gtgattgtaa caagcaacac caacattact   1500
aaagtaactg ttggatgtgt agaaacaaac gctcacgcag aaccactaaa acagagaatg   1560
gttaaaatac gttgcatgaa aaccatcaac cctacaacca aactaacacc gggaatgtta   1620
gcaaaatggc taagtacctg ggacagaata ccaatcaaac taaaccatga gatgcctgaa   1680
ctgtacttag gtaagtagcg tttggtaagt aacacatttt aaataccaac tttaaaacca   1740
acatcaattt atgaggttac tttactttac agagactact ggaccaaact cgagtgccac   1800
aactgccacg aagagtactg gcagcttaca acctactact gcaaggagtg cagaaagtgt   1860
gaacacggaa aactgcgata caccaaaaag gggtgcgagc agtgtgcctc cgaagcagca   1920
caagagacct cggcatgagt aaaagtaagt aacctactta aagtaaccta acaccatgac   1980
actttacttt gcttgtactt atgttacttt actttagttc ctcagcacta tcctgggaaa   2040
aagagaagtg ctccaagaca cgtgtttatt cagcaagcaa aaaagaagaa gcaaactaac   2100
cctgcggtgt accacggaga gaacaccata gaggaaatgg attctgctga acctgaacaa   2160
atggacactg agcaagcaac taaccaaact gctgaagctg gtggtggggg gggtgggggt   2220
ggtgggggtg gtggaggtgg tggggttggt aacagcactg gcggctttaa taacacaaca   2280
gaatttaaag taataaacaa tgaagtgtat attacttgtc acgctactag aatggtgcac   2340
atcaaccaag ctgacacaga tgaatactta atatttaatg ctggtagaac tactgatacc   2400
aaaacagctc aacagaaact aaacttagag tttttgtat atgatgattt tcaccaacaa    2460
gtaatgacac cttggtttct ggtagatagc aacgcttggg gtgtatggat gagtcctaaa   2520
gactttcaac aaatgaaaac actatgtagt gaaattagtt tggttacttt ggaacaagaa   2580
atagacaatg taaccataaa aactgtaaca gaaaccaacc aaggtaacgc atcaaccaag   2640
caatttaaca atgacttgac tgcgtcgtta caagttgctt tagatactaa caacataatg   2700
ccatatactc cagctgcgcc gttgggggaa acactagggt ttgttccttg gagagcaacc   2760
aaaccaaccc aatataggta ttatcatcca tgttacattt acaacagata tcctaacatt   2820
caaaaaatgg gttcagaaca attagagtgg caaggaatac aagatgatta ccttagtgtg   2880
gatgaacagt actttaactt tattactata gagaacaaca tacctattaa cattctcaga   2940
acgggtgata actttcatac aggcttatat gagtttaaaa gtaaaccatg taaactaacc   3000
ttaagctacc agagtacacg ttgcttgggt ttacctcctc tttgcaaacc aaagacagat   3060
```

-continued gcaacacaca aagtaacctc actagagaac ggagctgata tacaatacat acaaggagga 3120
gataatataa gactgggtca cttttggggt gaggagagag gtaagaagaa cgcagaaatg 3180
aacagagtta gaccttacaa cataggttac caatatcctg aatggatcat accagcaggg 3240
ttacagggta gttactttgc tggaggacca agacaatgga gtgacacaac caaagggggg 3300
gagtcacaca gtcagcagtt acaacagaac tttagtacta gatacatcta tgacaggaac 3360
cacggtggag acaaccaggt agacttatta gatgcaatac ccattcatga aagaagtaac 3420
tactactcag accatgaact agagcaacat acagcaaagc aaccaaagtt acatacacca 3480
ccggttcacc actcaaagat agactcgtgg gaagaggaag gttggcctgc tgcttcaggc 3540
acacactttg aagatgaggt tatatactta gattacttta actttagtgg tgaacaggag 3600
atagagtttc cacatgaagt attagatgat ggtgcacaga tgaaaaagct acttaactca 3660
taccaaccaa cagttgcttt agacaacgtt ggtcctgtat acccatgggg acaagtatgg 3720
gataagaaac ctgatgtgga tcacaaacct agcatgaaca acagcgctcc atttgtatgt 3780
aaaaacaatc ctccaggtca actctttgtt aaactaacag aaaacctcac tgatacattt 3840
aactatgatg aagatccaga cagaataaaa acttatggtt actttacttg gagaggcaag 3900
cttgtactaa aaggtaaact aagccaagta acatgctgga atcctgtcaa gagagaactc 3960
ataggagaac ctggtgtatt tagtaaagac aactatcaca aacagatacc aaacaacaaa 4020
ggtaactttg aaatagggtt acaatatgga agaagcacta tcaaatatat ctactaaagt 4080
aacctatgta atatgttact atgttactat gatgatatct caataaaagt tacatgaaga 4140
gtgaacaac 4149

<210> SEQ ID NO 18
<211> LENGTH: 4801
<212> TYPE: DNA
<213> ORGANISM: Aleutian mink disease virus

<400> SEQUENCE: 18
attaattctc aaccaatatt cgttagcaac caacaccagc tcgcttcgct cgcgcacctt 60
cggcgctggt gttgggcgct tcgcgcttgc taacttcata ttggttgaga attaatccgt 120
gtctttcctg tggaatgagg aagtagtgtg gtatataagc agaggttgct tggagcaaag 180
cacagaccgg ttacagcaaa gtaacatggc tcaggctcaa attgatgagc agaggagact 240
gcaggacctg tatgtgcagt tgaagaagga gattaacgac ggtgaaggag ttgcctggtt 300
gttccaacaa aagacctaca ccgacaagga caacaaacca accaaagcaa caccgccact 360
gaggacaacc tcttctgacc taaggttagc ttttgactct attgaagaga atttaacagc 420
ttctaatgaa cacttaacta acaatgagat aaacttttgt aaactaacct tggggaagac 480
gttgctgtta attgataagc atgtaaaaag ccacagatgg gatagtaaca aagttaactt 540
aatttggcaa atagaaaaag gaaaaactca gcaatttcat attcactgtt gcttaggtta 600
ctttgataag aatgaagatc ctaaggatgt tcaaaaatcc ttaggttggt ttatgaaaag 660
actaaataaa gacctagcag ttatctatag taaccatcat tgtgacatac aagatattaa 720
ggatcctgaa gatagagcta agaacctaaa agtgtggatt gaagatggac ctactaagcc 780
ttacaaatat tttaacaaac aaaccaaaca agactacaat aaaccagttc acttgagaga 840
ctatacattc atatacctgt ttaacaaaga taagataaat acagatagta tggatggtta 900
ctttgctgct ggtaacggtg gcattgttga caacctaact aacaaagaac gaaaaacttt 960
aagaaaaatg tacttagatg agcagagttc agatataatg gatgctaata tagactggga 1020

-continued

```
agatggccaa gacgcgccaa aagtaactga ccaaactgac tcagcaacca caaaaacagg   1080
aactagtttg atttggaaat catgtgctac taaagtaacc tcaaaaaaag aagttgctaa   1140
tccagttcag caaccttcta aaaaactgta ctcagctcaa agtactttag atgcattgtt   1200
taacgttggt tgctttactc cagaagatat gattataaag caaagtgaca aataccttga   1260
actatcttta gaaccaaacg ggcctcaaaa aattaacact ttacttcaca tgaaccaagt   1320
aaagacatca accatgatta ctgcttttga ttgtattata aaatttaatg aagaggaaga   1380
tgacaaacct ttgctagcaa ctataaaaga catgggactt aatgaacaat accttaagaa   1440
ggtactatgt accatcctaa ccaagcaagg tggaaagaga ggttgtattt ggttctatgg   1500
accgggggc actggaaaaa ccttgctagc atctttaata tgtaaagcaa cagtaaacta   1560
tggtatggtt actacaagca atccaaactt tccatggact gactgtggca atagaaacat   1620
catttgggct gaagagtgtg gtaactttgg taactgggtt gaagacttta aagccattac   1680
tggaggtggt gatgtaaaag tagacaccaa gaacaagcaa cctcaatcta ttaaaggctg   1740
tgtgattgta acaagcaaca ccaacataac caaagtaact gttggatgtg tggaaacaaa   1800
cgctcacgca gagccactta aacagaggat gattaagata cgttgcatga aaccatcaa   1860
ccctaaaact aaaataacac caggcatgtt aaaaagatgg ctaaatacct gggatagaca   1920
accaattcaa ctaagccatg agatgcctga actgtactta ggtaagtgcc gttggtaagt   1980
aacacatttt aaatgccaac tttaaaccaa catcaattta tgaggttact ttactttaca   2040
gagactactg gaccaaactc gagtgccaca actgccacga agaatactgg caactcacaa   2100
cctactactg caaagagtgc agaaagtgtg aacacggaaa actgcgacac accaaaaagg   2160
agtgcgagca gtgtgcctgc aaagcagcac aagagacctc ggcatgagta aaagtaaata   2220
acctacttaa agtaacctaa caccataaca ctttactttc cttgtactta tgttacttta   2280
ctttagttcc tcagcactat cctgggaaaa agagaagtgc tccaagacac gtgtttattc   2340
agcaagcaaa aaagaagaag caaactaacc ctgcggtcta ccacggagag gacaccatag   2400
aggaaatgga ttctactgaa gctgaacaaa tggacactga gcaagcaact aaccaaactg   2460
ctgaagctgg tggtgggggg ggtgggggtg gtgggggtgg tggtggtggt ggtggggttg   2520
gtaacagcac tggcggcttt aataacacaa cagaattcaa agtaataaac aatgaagtgt   2580
atattacttg tcacgctact agaatggtac acattaacca agctgacaca gacgaatact   2640
tgatatttaa tgctggtaga actactgata ccaaaacaca tcagcaaaaa ctaaacttag   2700
aattttttgt atatgatgat tttcaccaac aagtaatgac accttggtat atagtagata   2760
gcaacgcttg ggtgtatgg atgagtccta aagactttca acaaatgaaa acactgtgta   2820
gtgaaattag tttggttact ttggaacaag aaatagacaa tgtaaccata aaaactgtaa   2880
cagaaaccaa ccaaggtaac gcatctacca agcaattcaa caatgactta actgcgtcgt   2940
tacaggttgc tttagatact aacaacatac tgccatatac tccagctgcg ccgttggggg   3000
aaacactggg ctttgttcct tggagagcaa ccaaaccaac ccaatatagg tattatcatc   3060
catgttacat ttacaacaga tatcctaaca ttcaaaaagt tgcaacagaa acactaacct   3120
gggatgcagt acaagatgat taccttagtg tggatgaaca gtactttaac tttattacta   3180
tagagaacaa catacctatt aacattctca gaacgggaga taactttcat acaggcttgt   3240
atgagtttaa cagtaaacca tgtaaactaa ccttaagcta tcaaagtaca cgttgcttgg   3300
ggctacctcc tctctgcaaa ccaaagacag atacaacaca caaagtaacc tcaaaagaaa   3360
```

-continued

```
acggagctga cctaatttac atacaaggac aagataatac cagactaggt cacttttggg   3420
gtgaggaaag aggtaagaaa aacgcagaga tgaacagaat tagaccttac aacataggtt   3480
accaatatcc tgaatggata ataccagcag ggttacaggg tagttacttt gctggaggac   3540
caagacagtg gagtgacaca accaaaggtg caggtacaca cagtcaacac ttacaacaga   3600
actttagtac taggtacatc tatgacagaa accacggtgg agacaacgag gtagacctat   3660
tagatggaat acccattcat gaaagaagta actactactc agacaatgag atagagcaac   3720
atacagcaaa gcaaccaaag ttacgtacac cacccattca ccactcaaaa atagactcgt   3780
gggaagaaga aggttggcct gctgcttcag gcacacactt tgaagatgag gttatatacc   3840
tagactactt taactttagt ggtgaacagg agctaaactt tccacatgaa gtattagatg   3900
atgctgctca gatgaaaaag ctacttaact cataccaacc aacagttgct caagacaacg   3960
ttggtcctgt atacccgtgg ggacagatat gggacaagaa acctcatatg gatcacaaac   4020
ctagcatgaa caacaacgct ccatttgtat gtaaaaacaa ccctccaggt caactctttg   4080
ttaaactaac agaaaacctc actgatacat ttaactatga tgaaaatcca gacagaataa   4140
aaacctatgg ttactttact tggagaggca agcttgtact aaaaggcaaa ctaagccaag   4200
taacatgctg gaatcctgtt aagagagaac tcataggaga acctggtgta tttactaaag   4260
acaagtatca caaacagata ccaaacaaca aaggtaactt tgaaataggg ttacaatatg   4320
gaagaagtac tatcaaatat atctactaaa gtaacctgtg tactatgtta ctatgttact   4380
atgataatat ctcaataaaa gttacatgaa tagtgaacaa cctaaatact gtgtacttcc   4440
ttattttacc agaaagtggc ggattaaaat aaacctacat tctatactat ctatatacta   4500
ctaactaacc tataggttac tttgctttga tatactgatg taggaataca ggatactaac   4560
atttatatat atactaacat ctatactact aacctaacta tggcctaatg tatgcagtgt   4620
cggcgtcgcc gacaactaca ttatattatt aggcatagtt aggttagtag tatagatgtt   4680
agtatatata taaatgttag tatcctgtgt tcctacttca gtatataaag aaagtttcct   4740
ataggtgggt ttgcggtcta tctagagttg tggtccgtat tggtttctgt aaaggacctg   4800
a                                                                     4801
```

<210> SEQ ID NO 19
<211> LENGTH: 4174
<212> TYPE: DNA
<213> ORGANISM: Aleutian mink disease virus

<400> SEQUENCE: 19

```
ttttaacgac gggggaagga gttgcctggc tgttccagca aaagacctac accgacaaag     60
acaacaaacc aaccaaagca acaccaccac tgaggacaac ctcttctgat ctaaggttag    120
catttgaatc tattgaagaa aatttaaagt cttctactga acacttaact aacaatgaca    180
taaacttttg taaactaacc ttggggaagg cgttggtggc acttgataag catgtaagga    240
gccacagatg ggatgctaac aaagttaact ttatctggca aatagaaaaa ggatccacta    300
agcaacttca tattcactgt tgcttaggtt actttgataa aaatgaagat cctaaggatg    360
ttcaaaaatc cttaggttgg ttaattaaaa aaataaataa agacttagca gttatttata    420
gtaaccatca ttgtgacata caaaacatta cggatcctga agccaaagct aataacttga    480
aagtgtggat tgaagatggg cctactaaac cttacaagta ccatcacaaa caaaccaaac    540
aggaatacaa caaagcagtt cacatgcaag actataccat aatatatctg tttaacaaag    600
ataagataac tactgatagt atggatggtt actttgctgc tggtaacggt ggcattattg    660
```

-continued

```
acaacctaac taacaaggaa cgaaaatgtt taagaaaaat gtacttggat gagcagagtt    720
cagatataat ggatgctgac atagactggg aagatggcca agacgcgcca aaagtaactg    780
accaaactga ctcagcaacc acaaaaacag gaactagttt gatttggaaa tcatgtgcta    840
ccaaagtaac ctcaaaaaaa gaggttactg aaccagttaa gcaaccttct aaaaaactgt    900
gctcagctca aagtacttta gatgctttat ttgaccttgg ttgctttact ccagaagata    960
tgattataaa atgcagtgac aaatatcttg aactatcttt agaaccaaac ggacctcaaa   1020
aaattaacac tttacttcac atgaaccaag taaagacagc aagcatgatt agtgccttag   1080
attgtattgt aaaatttaat gaagaggaag atgatcaacc tttaatagca accataaaag   1140
atatgggact taatgaacaa caccttaaga aagtactgtg taccatacta accaagcaag   1200
gtggaaaaag aggttgtatt tggttttatg gaccaggagg tactggaaag acattgctag   1260
catccttact atgtagagca acagtaaact ttggtgtggt tactacaagc aatccaaact   1320
ttccatggac tgactgtggc aatagaaaca tcatctgggc tgaagaatgt ggtaaccttg   1380
gtaactgggt tgaagacttt aaagccatta ctggaggtgg tgatataaaa gtagacacca   1440
aaaacaagca acctcaatcc atcaaaggct gtgtgattgt aacaagcaac accaacatta   1500
ctaaagtaac tgttggatgt gtagaaacaa acgctcacgc agaaccacta aaacagagaa   1560
tggttaaaat acgttgcatg aaaaccatca accctacaac caaactaaca ccgggaatgt   1620
tagcaaaatg gctaagtacc tgggacagaa taccaatcaa actaaaccat gagatgcctg   1680
aactgtactt aggtaagtag cgtttggtaa gtaacacatt ttaaatacca actttaaaac   1740
caacatcaat ttatgaggtt actttacttt acagagacta ctggaccaaa ctcgagtgcc   1800
acaactgcca cgaagagtac tggcagctta caacctacta ctgcaaggag tgcagaaagt   1860
gtgaacacgg aaaactgcga tacaccaaaa aggggtgcga gcagtgtgcc tccgaagcag   1920
cacaagagac ctcggcatga gtaaaagtaa gtaacctact taaagtaacc taacaccatg   1980
acactttact ttgcttgtac ttatgttact ttactttagt tcctcagcac tatcctggga   2040
aaaagagaag tgctccaaga cacgtgttta ttcagcaagc aaaaaagaag aagcaaacta   2100
accctgcggt gtaccacgga gagaacacca tagaggaaat ggattctgct gaacctgaac   2160
aaatggacac tgagcaagca actaaccaaa ctgctgaagc tggtggtggg gggggtgggg   2220
gtggtggggg tggtggaggt ggtggggttg gtaacagcac tggcggcttt aataacacaa   2280
cagaatttaa agtaataaac aatgaagtgt atattacttg tcacgctact agaatggtgc   2340
acatcaacca agctgacaca gatgaatact taatatttaa tgctggtaga actactgata   2400
ccaaaacagc tcaacagaaa ctaaacttag agtttttttgt atatgatgat tttcaccaac   2460
aagtaatgac accttggttt ctggtagata gcaacgcttg gggtgtatgg atgagtccta   2520
aagactttca acaaatgaaa acactatgta gtgaaattag tttggttact ttggaacaag   2580
aaatagacaa tgtaaccata aaaactgtaa cagaaaccaa ccaaggtaac gcatcaacca   2640
agcaatttaa caatgacttg actgcgtcgt tacaagttgc tttagatact aacaacataa   2700
tgccatatac tccagctgcg ccgttggggg aaacactagg gtttgttcct tggagagcaa   2760
ccaaaccaac ccaatatagg tattatcatc catgttacat ttacaacaga tatcctaaca   2820
ttcaaaaaat gggttcagaa caattagagt ggcaaggaat acaagatgat taccttagtg   2880
tggatgaaca gtactttaac tttattacta tagagaacaa catacctatt aacattctca   2940
gaacgggtga taactttcat acaggcttat atgagtttaa aagtaaacca tgtaaactaa   3000
```

-continued

```
ccttaagcta ccagagtaca cgttgcttgg gtttacctcc tctttgcaaa ccaaagacag   3060

atgcaacaca caaagtaacc tcactagaga acggagctga tatacaatac atacaaggag   3120

gagataatat aagactgggt cacttttggg gtgaggagag aggtaagaag aacgcagaaa   3180

tgaacagagt tagaccttac aacataggtt accaatatcc tgaatggatc ataccagcag   3240

ggttacaggg tagttacttt gctggaggac caagacaatg gagtgacaca accaaagggg   3300

gggagtcaca cagtcagcag ttacaacaga actttagtac tagatacatc tatgacagga   3360

accacggtgg agacaaccag gtagacttat tagatgcaat acccattcat gaaagaagta   3420

actactactc agaccatgaa ctagagcaac atacagcaaa gcaaccaaag ttacatacac   3480

caccggttca ccactcaaag atagactcgt gggaagagga aggttggcct gctgcttcag   3540

gcacacactt tgaagatgag gttatatact tagattactt taactttagt ggtgaacagg   3600

agatagagtt tccacatgaa gtattagatg atggtgcaca gatgaaaaag ctacttaact   3660

cataccaacc aacagttgct ttagacaacg ttggtcctgt atacccatgg ggacaagtat   3720

gggataagaa acctgatgtg gatcacaaac ctagcatgaa caacagcgct ccatttgtat   3780

gtaaaaacaa tcctccaggt caactctttg ttaaactaac agaaaacctc actgatacat   3840

ttaactatga tgaagatcca gacagaataa aaacttatgg ttactttact tggagaggca   3900

agcttgtact aaaaggtaaa ctaagccaag taacatgctg gaatcctgtc aagagagaac   3960

tcataggaga acctggtgta tttagtaaag acaactatca caaacagata ccaaacaaca   4020

aaggtaactt tgaaataggg ttacaatatg gaagaagcac tatcaaatat atctactaaa   4080

gtaacctatg taatatgtta ctatgttact atgatgatat ctcaataaaa gttacatgaa   4140

gagtgaacaa ctatgggggg gggtccccaa aaaa                               4174
```

```
<210> SEQ ID NO 20
<211> LENGTH: 565
<212> TYPE: PRT
<213> ORGANISM: Aleutian mink disease virus

<400> SEQUENCE: 20

Leu Thr Thr Gly Glu Gly Val Ala Trp Leu Phe Gln Gln Lys Thr Tyr
1               5                   10                  15

Thr Asp Lys Asp Asn Lys Pro Thr Lys Ala Thr Pro Pro Leu Arg Thr
            20                  25                  30

Thr Ser Ser Asp Leu Arg Leu Ala Phe Glu Ser Ile Glu Glu Asn Leu
        35                  40                  45

Lys Ser Ser Thr Glu His Leu Thr Asn Asn Asp Ile Asn Phe Cys Lys
    50                  55                  60

Leu Thr Leu Gly Lys Ala Leu Val Ala Leu Asp Lys His Val Arg Ser
65                  70                  75                  80

His Arg Trp Asp Ala Asn Lys Val Asn Phe Ile Trp Gln Ile Glu Lys
                85                  90                  95

Gly Ser Thr Lys Gln Leu His Ile His Cys Cys Leu Gly Tyr Phe Asp
            100                 105                 110

Lys Asn Glu Asp Pro Lys Asp Val Gln Lys Ser Leu Gly Trp Leu Ile
        115                 120                 125

Lys Lys Ile Asn Lys Asp Leu Ala Val Ile Tyr Ser Asn His His Cys
    130                 135                 140

Asp Ile Gln Asn Ile Thr Asp Pro Glu Ala Lys Ala Asn Asn Leu Lys
145                 150                 155                 160

Val Trp Ile Glu Asp Gly Pro Thr Lys Pro Tyr Lys Tyr His His Lys
```

```
                165                 170                 175

Gln Thr Lys Gln Glu Tyr Asn Lys Ala Val His Met Gln Asp Tyr Thr
            180                 185                 190

Ile Ile Tyr Leu Phe Asn Lys Asp Lys Ile Thr Thr Asp Ser Met Asp
        195                 200                 205

Gly Tyr Phe Ala Ala Gly Asn Gly Gly Ile Ile Asp Asn Leu Thr Asn
    210                 215                 220

Lys Glu Arg Lys Cys Leu Arg Lys Met Tyr Leu Asp Glu Gln Ser Ser
225                 230                 235                 240

Asp Ile Met Asp Ala Asp Ile Asp Trp Glu Asp Gly Gln Asp Ala Pro
                245                 250                 255

Lys Val Thr Asp Gln Thr Asp Ser Ala Thr Thr Lys Thr Gly Thr Ser
            260                 265                 270

Leu Ile Trp Lys Ser Cys Ala Thr Lys Val Thr Ser Lys Lys Glu Val
        275                 280                 285

Thr Glu Pro Val Lys Gln Pro Ser Lys Lys Leu Cys Ser Ala Gln Ser
    290                 295                 300

Thr Leu Asp Ala Leu Phe Asp Leu Gly Cys Phe Thr Pro Glu Asp Met
305                 310                 315                 320

Ile Ile Lys Cys Ser Asp Lys Tyr Leu Glu Leu Ser Leu Glu Pro Asn
                325                 330                 335

Gly Pro Gln Lys Ile Asn Thr Leu Leu His Met Asn Gln Val Lys Thr
            340                 345                 350

Ala Ser Met Ile Ser Ala Leu Asp Cys Ile Val Lys Phe Asn Glu Glu
        355                 360                 365

Glu Asp Asp Gln Pro Leu Ile Ala Thr Ile Lys Asp Met Gly Leu Asn
    370                 375                 380

Glu Gln His Leu Lys Lys Val Leu Cys Thr Ile Leu Thr Lys Gln Gly
385                 390                 395                 400

Gly Lys Arg Gly Cys Ile Trp Phe Tyr Gly Pro Gly Gly Thr Gly Lys
                405                 410                 415

Thr Leu Leu Ala Ser Leu Leu Cys Arg Ala Thr Val Asn Phe Gly Val
            420                 425                 430

Val Thr Thr Ser Asn Pro Asn Phe Pro Trp Thr Asp Cys Gly Asn Arg
        435                 440                 445

Asn Ile Ile Trp Ala Glu Glu Cys Gly Asn Leu Gly Asn Trp Val Glu
    450                 455                 460

Asp Phe Lys Ala Ile Thr Gly Gly Gly Asp Ile Lys Val Asp Thr Lys
465                 470                 475                 480

Asn Lys Gln Pro Gln Ser Ile Lys Gly Cys Val Ile Val Thr Ser Asn
                485                 490                 495

Thr Asn Ile Thr Lys Val Thr Val Gly Cys Val Glu Thr Asn Ala His
            500                 505                 510

Ala Glu Pro Leu Lys Gln Arg Met Val Lys Ile Arg Cys Met Lys Thr
        515                 520                 525

Ile Asn Pro Thr Thr Lys Leu Thr Pro Gly Met Leu Ala Lys Trp Leu
    530                 535                 540

Ser Thr Trp Asp Arg Ile Pro Ile Lys Leu Asn His Glu Met Pro Glu
545                 550                 555                 560

Leu Tyr Leu Gly Lys
                565

<210> SEQ ID NO 21
```

<211> LENGTH: 701
<212> TYPE: PRT
<213> ORGANISM: Aleutian mink disease virus

<400> SEQUENCE: 21

```
His His Asp Thr Leu Leu Cys Leu Tyr Leu Cys Tyr Phe Thr Leu Val
1               5                   10                  15

Pro Gln His Tyr Pro Gly Lys Lys Arg Ser Ala Pro Arg His Val Phe
            20                  25                  30

Ile Gln Gln Ala Lys Lys Lys Lys Gln Thr Asn Pro Ala Val Tyr His
        35                  40                  45

Gly Glu Asn Thr Ile Glu Glu Met Asp Ser Ala Glu Pro Glu Gln Met
    50                  55                  60

Asp Thr Glu Gln Ala Thr Asn Gln Thr Ala Glu Ala Gly Gly Gly Gly
65                  70                  75                  80

Gly Gly Gly Gly Gly Gly Gly Gly Gly Gly Gly Val Gly Asn Ser Thr
                85                  90                  95

Gly Gly Phe Asn Asn Thr Thr Glu Phe Lys Val Ile Asn Asn Glu Val
            100                 105                 110

Tyr Ile Thr Cys His Ala Thr Arg Met Val His Ile Asn Gln Ala Asp
        115                 120                 125

Thr Asp Glu Tyr Leu Ile Phe Asn Ala Gly Arg Thr Thr Asp Thr Lys
    130                 135                 140

Thr Ala Gln Gln Lys Leu Asn Leu Glu Phe Phe Val Tyr Asp Asp Phe
145                 150                 155                 160

His Gln Gln Val Met Thr Pro Trp Phe Leu Val Asp Ser Asn Ala Trp
                165                 170                 175

Gly Val Trp Met Ser Pro Lys Asp Phe Gln Gln Met Lys Thr Leu Cys
            180                 185                 190

Ser Glu Ile Ser Leu Val Thr Leu Glu Gln Glu Ile Asp Asn Val Thr
        195                 200                 205

Ile Lys Thr Val Thr Glu Thr Asn Gln Gly Asn Ala Ser Thr Lys Gln
    210                 215                 220

Phe Asn Asn Asp Leu Thr Ala Ser Leu Gln Val Ala Leu Asp Thr Asn
225                 230                 235                 240

Asn Ile Met Pro Tyr Thr Pro Ala Ala Pro Leu Gly Glu Thr Leu Gly
                245                 250                 255

Phe Val Pro Trp Arg Ala Thr Lys Pro Thr Gln Tyr Arg Tyr Tyr His
            260                 265                 270

Pro Cys Tyr Ile Tyr Asn Arg Tyr Pro Asn Ile Gln Lys Met Gly Ser
        275                 280                 285

Glu Gln Leu Glu Trp Gln Gly Ile Gln Asp Asp Tyr Leu Ser Val Asp
    290                 295                 300

Glu Gln Tyr Phe Asn Phe Ile Thr Ile Glu Asn Asn Ile Pro Ile Asn
305                 310                 315                 320

Ile Leu Arg Thr Gly Asp Asn Phe His Thr Gly Leu Tyr Glu Phe Lys
                325                 330                 335

Ser Lys Pro Cys Lys Leu Thr Leu Ser Tyr Gln Ser Thr Arg Cys Leu
            340                 345                 350

Gly Leu Pro Pro Leu Cys Lys Pro Lys Thr Asp Ala Thr His Lys Val
        355                 360                 365

Thr Ser Leu Glu Asn Gly Ala Asp Ile Gln Tyr Ile Gln Gly Gly Asp
    370                 375                 380

Asn Ile Arg Leu Gly His Phe Trp Gly Glu Glu Arg Gly Lys Lys Asn
```

385 390 395 400

Ala Glu Met Asn Arg Val Arg Pro Tyr Asn Ile Gly Tyr Gln Tyr Pro
405 410 415

Glu Trp Ile Ile Pro Ala Gly Leu Gln Gly Ser Tyr Phe Ala Gly Gly
420 425 430

Pro Arg Gln Trp Ser Asp Thr Thr Lys Gly Gly Glu Ser His Ser Gln
435 440 445

Gln Leu Gln Gln Asn Phe Ser Thr Arg Tyr Ile Tyr Asp Arg Asn His
450 455 460

Gly Gly Asp Asn Gln Val Asp Leu Leu Asp Ala Ile Pro Ile His Glu
465 470 475 480

Arg Ser Asn Tyr Tyr Ser Asp His Glu Leu Glu Gln His Thr Ala Lys
485 490 495

Gln Pro Lys Leu His Thr Pro Pro Val His His Ser Lys Ile Asp Ser
500 505 510

Trp Glu Glu Glu Gly Trp Pro Ala Ala Ser Gly Thr His Phe Glu Asp
515 520 525

Glu Val Ile Tyr Leu Asp Tyr Phe Asn Phe Ser Gly Glu Gln Glu Ile
530 535 540

Glu Phe Pro His Glu Val Leu Asp Asp Gly Ala Gln Met Lys Lys Leu
545 550 555 560

Leu Asn Ser Tyr Gln Pro Thr Val Ala Leu Asp Asn Val Gly Pro Val
565 570 575

Tyr Pro Trp Gly Gln Val Trp Asp Lys Lys Pro Asp Val Asp His Lys
580 585 590

Pro Ser Met Asn Asn Ser Ala Pro Phe Val Cys Lys Asn Asn Pro Pro
595 600 605

Gly Gln Leu Phe Val Lys Leu Thr Glu Asn Leu Thr Asp Thr Phe Asn
610 615 620

Tyr Asp Glu Asp Pro Asp Arg Ile Lys Thr Tyr Gly Tyr Phe Thr Trp
625 630 635 640

Arg Gly Lys Leu Val Leu Lys Gly Lys Leu Ser Gln Val Thr Cys Trp
645 650 655

Asn Pro Val Lys Arg Glu Leu Ile Gly Glu Pro Gly Val Phe Ser Lys
660 665 670

Asp Asn Tyr His Lys Gln Ile Pro Asn Asn Lys Gly Asn Phe Glu Ile
675 680 685

Gly Leu Gln Tyr Gly Arg Ser Thr Ile Lys Tyr Ile Tyr
690 695 700

<210> SEQ ID NO 22
<211> LENGTH: 240
<212> TYPE: PRT
<213> ORGANISM: Aleutian mink disease virus

<400> SEQUENCE: 22

Arg Met Val His Ile Asn Gln Ala Asp Thr Asp Glu Tyr Leu Ile Phe
1 5 10 15

Asn Ala Gly Arg Thr Thr Asp Thr Lys Thr His Gln Gln Lys Leu Asn
20 25 30

Leu Glu Phe Phe Val Tyr Asp Asp Phe His Gln Gln Val Met Thr Pro
35 40 45

Trp Tyr Ile Val Asp Ser Asn Ala Trp Gly Val Trp Met Ser Pro Lys
50 55 60

-continued

```
Asp Phe Gln Gln Met Lys Thr Leu Cys Ser Glu Ile Ser Leu Val Thr
65                  70                  75                  80

Leu Glu Gln Glu Ile Asp Asn Val Thr Ile Lys Thr Val Thr Glu Thr
                85                  90                  95

Asn Gln Gly Asn Ala Ser Thr Lys Gln Phe Asn Asn Asp Leu Thr Ala
            100                 105                 110

Ser Leu Gln Val Ala Leu Asp Thr Asn Asn Ile Leu Pro Tyr Thr Pro
        115                 120                 125

Ala Ala Pro Leu Gly Glu Thr Leu Gly Phe Val Pro Trp Arg Ala Thr
    130                 135                 140

Lys Pro Thr Gln Tyr Arg Tyr Tyr His Pro Cys Tyr Ile Tyr Asn Arg
145                 150                 155                 160

Tyr Pro Asn Ile Gln Lys Val Ala Thr Glu Thr Leu Thr Trp Asp Ala
                165                 170                 175

Val Gln Asp Asp Tyr Leu Ser Val Asp Glu Gln Tyr Phe Asn Phe Ile
            180                 185                 190

Thr Ile Glu Asn Asn Ile Pro Ile Asn Ile Leu Arg Thr Gly Asp Asn
        195                 200                 205

Phe His Thr Gly Leu Tyr Glu Phe Asn Ser Lys Pro Cys Lys Leu Thr
    210                 215                 220

Leu Ser Tyr Gln Ser Thr Arg Cys Leu Gly Leu Pro Pro Leu Cys Lys
225                 230                 235                 240


<210> SEQ ID NO 23
<211> LENGTH: 240
<212> TYPE: PRT
<213> ORGANISM: Aleutian mink disease virus

<400> SEQUENCE: 23

Arg Met Val His Ile Asn Gln Ala Asp Thr Asp Glu Tyr Leu Ile Phe
1               5                   10                  15

Asn Ala Gly Arg Thr Thr Asp Thr Lys Thr His Gln Gln Lys Leu Asn
            20                  25                  30

Leu Glu Phe Phe Val Tyr Asp Asp Phe His Gln Gln Val Met Thr Pro
        35                  40                  45

Trp Tyr Ile Val Asp Ser Asn Ala Trp Gly Val Trp Met Ser Pro Lys
    50                  55                  60

Asp Phe Gln Gln Met Lys Thr Leu Cys Ser Glu Ile Ser Leu Val Thr
65                  70                  75                  80

Leu Glu Gln Glu Ile Asp Asn Val Thr Ile Lys Thr Val Thr Glu Thr
                85                  90                  95

Asn Gln Gly Asn Ala Ser Thr Lys Gln Phe Asn Asn Asp Leu Thr Ala
            100                 105                 110

Ser Leu Gln Val Ala Leu Asp Thr Asn Asn Ile Leu Pro Tyr Thr Pro
        115                 120                 125

Ala Ala Pro Leu Gly Glu Thr Leu Gly Phe Val Pro Trp Arg Ala Thr
    130                 135                 140

Lys Pro Thr Gln Tyr Arg Tyr Tyr His Pro Cys Tyr Ile Tyr Asn Arg
145                 150                 155                 160

Tyr Pro Asn Ile Gln Lys Val Ala Thr Glu Thr Leu Thr Trp Asp Ala
                165                 170                 175

Val Gln Asp Asp Tyr Leu Ser Val Asp Glu Gln Tyr Phe Asn Phe Ile
            180                 185                 190

Thr Ile Glu Asn Asn Ile Pro Ile Asn Ile Leu Arg Thr Gly Asp Asn
        195                 200                 205
```

Phe His Thr Gly Leu Tyr Glu Phe Asn Ser Lys Pro Cys Lys Leu Thr
210 215 220

Leu Ser Tyr Gln Ser Thr Arg Cys Leu Gly Leu Pro Pro Leu Cys Lys
225 230 235 240

<210> SEQ ID NO 24
<211> LENGTH: 240
<212> TYPE: PRT
<213> ORGANISM: Aleutian mink disease virus

<400> SEQUENCE: 24

Arg Met Val His Ile Asn Gln Ala Asp Thr Asp Glu Tyr Leu Ile Phe
1 5 10 15

Asn Ala Gly Arg Thr Thr Asp Thr Lys Thr His Gln Gln Lys Leu Asn
20 25 30

Leu Glu Phe Phe Val Tyr Asp Asp Phe His Gln Gln Val Met Thr Pro
35 40 45

Trp Tyr Ile Val Asp Ser Asn Ala Trp Gly Val Trp Met Ser Pro Lys
50 55 60

Asp Phe Gln Gln Met Lys Thr Leu Cys Ser Glu Ile Ser Leu Val Thr
65 70 75 80

Leu Glu Gln Glu Ile Asp Asn Val Thr Ile Lys Thr Val Thr Glu Thr
85 90 95

Asn Gln Gly Asn Ala Ser Thr Lys Gln Phe Asn Asn Asp Leu Thr Ala
100 105 110

Ser Leu Gln Val Ala Leu Asp Thr Asn Asn Ile Leu Pro Tyr Thr Pro
115 120 125

Ala Ala Pro Leu Gly Glu Thr Leu Gly Phe Val Pro Trp Arg Ala Thr
130 135 140

Lys Pro Thr Gln Tyr Arg Tyr Tyr His Pro Cys Tyr Ile Tyr Asn Arg
145 150 155 160

Tyr Pro Asn Ile Gln Lys Val Ala Thr Glu Thr Leu Thr Trp Asp Ala
165 170 175

Val Gln Asp Asp Tyr Leu Ser Val Asp Glu Gln Tyr Phe Asn Phe Ile
180 185 190

Thr Ile Glu Asn Asn Ile Pro Ile Asn Ile Leu Arg Thr Gly Asp Asn
195 200 205

Phe His Thr Gly Leu Tyr Glu Phe Asn Ser Lys Pro Cys Lys Leu Thr
210 215 220

Leu Ser Tyr Gln Ser Thr Arg Cys Leu Gly Leu Pro Pro Leu Cys Lys
225 230 235 240

<210> SEQ ID NO 25
<211> LENGTH: 240
<212> TYPE: PRT
<213> ORGANISM: Aleutian mink disease virus

<400> SEQUENCE: 25

Arg Met Val His Ile Asn Gln Ala Asp Thr Asp Glu Tyr Leu Ile Phe
1 5 10 15

Asn Ala Gly Arg Thr Thr Asp Thr Lys Thr His Gln Gln Lys Leu Asn
20 25 30

Leu Glu Phe Phe Val Tyr Asp Asp Phe His Gln Gln Val Met Thr Pro
35 40 45

Trp Tyr Leu Val Asp Ser Asn Ala Trp Gly Val Trp Met Ser Pro Lys
50 55 60

```
Asp Phe Gln Gln Met Lys Thr Leu Cys Ser Glu Ile Ser Leu Leu Ser
65                  70                  75                  80

Leu Glu Gln Glu Ile Asp Asn Val Thr Ile Lys Thr Val Thr Glu Thr
                85                  90                  95

Asn Gln Gly Asn Ala Ser Thr Lys Gln Phe Asn Asn Asp Leu Thr Ala
            100                 105                 110

Ser Leu Gln Val Ala Leu Asp Thr Asn Asn Ile Leu Pro Tyr Thr Pro
        115                 120                 125

Ala Ala Pro Leu Gly Glu Thr Leu Gly Phe Val Pro Trp Arg Ala Thr
    130                 135                 140

Lys Pro Thr Gln Tyr Arg Tyr Tyr His Pro Cys Tyr Ile Tyr Asn Arg
145                 150                 155                 160

Tyr Pro Asn Ile Gln Lys Val Ala Gly Glu Thr Leu Thr Trp Asp Ala
                165                 170                 175

Val Gln Asp Asp Tyr Leu Ser Val Asp Glu Gln Tyr Phe Asn Phe Ile
            180                 185                 190

Thr Ile Glu Asn Asn Ile Pro Ile Asn Ile Leu Arg Thr Gly Asp Asn
        195                 200                 205

Phe His Thr Gly Leu Tyr Glu Phe Asn Ser Lys Pro Cys Lys Leu Thr
    210                 215                 220

Leu Ser Tyr Gln Ser Thr Arg Cys Leu Gly Leu Pro Pro Leu Cys Lys
225                 230                 235                 240


<210> SEQ ID NO 26
<211> LENGTH: 240
<212> TYPE: PRT
<213> ORGANISM: Aleutian mink disease virus

<400> SEQUENCE: 26

Arg Met Val His Ile Asn Gln Ala Asp Thr Asp Glu Tyr Leu Ile Phe
1               5                   10                  15

Asn Ala Gly Arg Thr Thr Asp Thr Lys Thr His Gln Gln Lys Leu Asn
            20                  25                  30

Leu Glu Phe Phe Val Tyr Asp Asp Phe His Gln Gln Val Met Thr Pro
        35                  40                  45

Trp Tyr Ile Val Asp Ser Asn Ala Trp Gly Val Trp Met Ser Pro Lys
    50                  55                  60

Asp Phe Gln Gln Met Lys Thr Leu Cys Ser Glu Ile Ser Leu Val Thr
65                  70                  75                  80

Leu Glu Gln Glu Ile Asp Asn Val Thr Ile Lys Thr Val Thr Glu Thr
                85                  90                  95

Asn Gln Gly Asn Ala Ser Thr Lys Gln Phe Asn Asn Asp Leu Thr Ala
            100                 105                 110

Ser Leu Gln Val Ala Leu Asp Thr Asn Asn Ile Leu Pro Tyr Thr Pro
        115                 120                 125

Ala Ala Pro Leu Gly Glu Thr Leu Gly Phe Val Pro Trp Arg Ala Thr
    130                 135                 140

Lys Pro Thr Gln Tyr Arg Tyr Tyr His Pro Cys Tyr Ile Tyr Asn Arg
145                 150                 155                 160

Tyr Pro Asn Ile Gln Lys Val Ala Thr Glu Thr Leu Thr Trp Asp Ala
                165                 170                 175

Val Gln Asp Asp Tyr Leu Ser Val Asp Glu Gln Tyr Phe Asn Phe Ile
            180                 185                 190

Thr Ile Glu Asn Asn Ile Pro Ile Asn Ile Leu Arg Thr Gly Asp Asn
```

```
        195                 200                 205

Phe His Thr Gly Leu Tyr Glu Phe Asn Ser Lys Pro Cys Lys Leu Thr
    210                 215                 220

Leu Ser Tyr Gln Ser Thr Arg Cys Leu Gly Leu Pro Pro Leu Cys Lys
225                 230                 235                 240


<210> SEQ ID NO 27
<211> LENGTH: 240
<212> TYPE: PRT
<213> ORGANISM: Aleutian mink disease virus

<400> SEQUENCE: 27

Arg Met Val His Ile Asn Gln Ala Asp Thr Asp Glu Tyr Leu Ile Phe
1               5                   10                  15

Asn Ala Asp Arg Thr Thr Asp Thr Lys Thr Ala Gln Lys Lys Leu Asn
            20                  25                  30

Leu Glu Phe Phe Val Tyr Asp Asp Phe His Gln Gln Val Met Thr Pro
        35                  40                  45

Trp Phe Ile Val Asp Ser Asn Ala Trp Gly Val Trp Met Ser Pro Lys
    50                  55                  60

Asp Phe Gln Gln Met Lys Thr Leu Cys Ser Glu Ile Ser Leu Val Thr
65                  70                  75                  80

Leu Glu Gln Glu Ile Asp Asn Val Thr Ile Lys Thr Val Thr Glu Thr
                85                  90                  95

Asn Gln Gly Asn Ala Ser Thr Lys Gln Phe Asn Asn Asp Leu Thr Ala
            100                 105                 110

Ser Leu Gln Val Ala Leu Asp Thr Asn Asn Ile Leu Pro Tyr Thr Pro
        115                 120                 125

Ala Ala Pro Leu Gly Glu Thr Leu Gly Phe Val Pro Trp Arg Ala Thr
    130                 135                 140

Lys Pro Thr Gln Tyr Arg Tyr Tyr His Pro Cys Tyr Ile Tyr Asn Arg
145                 150                 155                 160

Tyr Pro Asn Ile Gln Lys Leu Gly Gln Glu Gln Leu Glu Trp Thr Gly
                165                 170                 175

Thr Gln Asp Asp Tyr Leu Ser Val Asp Glu Gln Tyr Phe Asn Phe Ile
            180                 185                 190

Thr Ile Glu Asn Asn Ile Pro Ile Asn Ile Leu Arg Thr Gly Asp Asn
        195                 200                 205

Phe His Thr Gly Leu Tyr Glu Phe Asn Ser Lys Pro Cys Lys Leu Thr
    210                 215                 220

Leu Ser Tyr Gln Ser Thr Arg Cys Leu Gly Leu Pro Pro Leu Cys Lys
225                 230                 235                 240


<210> SEQ ID NO 28
<211> LENGTH: 240
<212> TYPE: PRT
<213> ORGANISM: Aleutian mink disease virus

<400> SEQUENCE: 28

Arg Met Val His Ile Asn Gln Ala Asp Thr Asp Glu Tyr Leu Ile Phe
1               5                   10                  15

Asn Ala Gly Arg Thr Thr Asp Thr Lys Thr Ala Gln Lys Lys Leu Asn
            20                  25                  30

Leu Glu Phe Phe Val Tyr Asp Asp Phe His Gln Gln Val Met Thr Pro
        35                  40                  45

Trp Phe Ile Val Asp Ser Asn Ala Trp Gly Val Trp Met Ser Pro Lys
```

```
    50                  55                  60

Asp Phe Gln Gln Met Lys Thr Leu Cys Ser Glu Ile Ser Leu Val Thr
65                  70                  75                  80

Leu Glu Gln Glu Ile Asp Asn Val Thr Ile Lys Thr Val Thr Glu Thr
                85                  90                  95

Asn Gln Gly Asn Ala Ser Thr Lys Gln Phe Asn Asn Asp Leu Thr Ala
            100                 105                 110

Ser Leu Gln Val Ala Leu Asp Thr Asn Asn Ile Leu Pro Tyr Thr Pro
        115                 120                 125

Ala Ala Pro Leu Gly Glu Thr Leu Gly Phe Val Pro Trp Arg Ala Thr
    130                 135                 140

Lys Pro Thr Gln Tyr Arg Tyr Tyr His Pro Cys Tyr Ile Tyr Asn Arg
145                 150                 155                 160

Tyr Pro Asn Ile Gln Lys Met Gly Gln Glu Gln Leu Glu Trp Thr Gly
                165                 170                 175

Thr Gln Asp Asp Tyr Leu Ser Val Asp Glu Gln Tyr Phe Asn Phe Ile
            180                 185                 190

Thr Ile Glu Asn Asn Ile Pro Ile Asn Ile Leu Arg Thr Gly Asp Asn
        195                 200                 205

Phe His Thr Gly Leu Tyr Glu Phe Asn Ser Lys Pro Cys Lys Leu Thr
    210                 215                 220

Leu Ser Tyr Gln Ser Thr Arg Cys Leu Gly Leu Pro Pro Leu Cys Lys
225                 230                 235                 240


<210> SEQ ID NO 29
<211> LENGTH: 240
<212> TYPE: PRT
<213> ORGANISM: Aleutian mink disease virus

<400> SEQUENCE: 29

Arg Met Val His Ile Asn Gln Ala Asp Thr Asp Glu Tyr Leu Ile Phe
1               5                   10                  15

Asn Ala Gly Arg Thr Thr Asp Thr Lys Thr Ala Gln Gln Lys Leu Asn
            20                  25                  30

Leu Glu Phe Phe Val Tyr Asp Asp Phe His Gln Gln Val Met Thr Pro
        35                  40                  45

Trp Phe Leu Val Asp Ser Asn Ala Trp Gly Val Trp Met Ser Pro Lys
    50                  55                  60

Asp Phe Gln Gln Met Lys Thr Leu Cys Ser Glu Ile Ser Leu Val Thr
65                  70                  75                  80

Leu Glu Gln Glu Ile Asp Asn Val Thr Ile Lys Thr Val Thr Glu Thr
                85                  90                  95

Asn Gln Gly Asn Ala Ser Thr Lys Gln Phe Asn Asn Asp Leu Thr Ala
            100                 105                 110

Ser Leu Gln Val Ala Leu Asp Thr Asn Asn Ile Met Pro Tyr Thr Pro
        115                 120                 125

Ala Ala Pro Leu Gly Glu Thr Leu Gly Phe Val Pro Trp Arg Ala Thr
    130                 135                 140

Lys Pro Thr Gln Tyr Arg Tyr Tyr His Pro Cys Tyr Ile Tyr Asn Arg
145                 150                 155                 160

Tyr Pro Asn Ile Gln Lys Met Gly Ser Glu Gln Leu Glu Trp Gln Gly
                165                 170                 175

Ile Gln Asp Asp Tyr Leu Ser Val Asp Glu Gln Tyr Phe Asn Phe Ile
            180                 185                 190
```

-continued

```
Thr Ile Glu Asn Asn Ile Pro Ile Asn Ile Leu Arg Thr Gly Asp Asn
        195                 200                 205

Phe His Thr Gly Leu Tyr Glu Phe Lys Ser Lys Pro Cys Lys Leu Thr
    210                 215                 220

Leu Ser Tyr Gln Ser Thr Arg Cys Leu Gly Leu Pro Pro Leu Cys Lys
225                 230                 235                 240


<210> SEQ ID NO 30
<211> LENGTH: 240
<212> TYPE: PRT
<213> ORGANISM: Aleutian mink disease virus

<400> SEQUENCE: 30

Arg Met Val His Ile Asn Gln Ala Asp Thr Asp Glu Tyr Leu Ile Phe
1               5                   10                  15

Asn Ala Gly Arg Thr Thr Asp Thr Lys Thr Ala Gln Pro Lys Leu Asn
            20                  25                  30

Leu Glu Phe Phe Val Tyr Asp Asp Phe His Gln Gln Val Met Thr Pro
        35                  40                  45

Trp Phe Met Val Asp Ser Asn Ala Trp Gly Val Trp Met Ser Pro Lys
    50                  55                  60

Asp Phe Gln Gln Met Lys Thr Leu Cys Ser Glu Ile Ser Leu Val Thr
65                  70                  75                  80

Leu Glu Gln Glu Ile Asp Asn Val Thr Ile Lys Thr Val Thr Glu Thr
                85                  90                  95

Asn Gln Gly Asn Ala Thr Val Lys Gln Tyr Asn Asn Asp Leu Thr Ala
            100                 105                 110

Ser Leu Gln Val Ala Leu Asp Thr Asn Asn Ile Leu Pro Tyr Thr Pro
        115                 120                 125

Ala Ala Pro Leu Gly Glu Thr Leu Gly Phe Val Pro Trp Arg Ala Thr
    130                 135                 140

Lys Pro Thr Gln Tyr Arg Tyr Tyr His Pro Cys Tyr Ile Tyr Asn Arg
145                 150                 155                 160

Tyr Pro Asn Ile Gln Lys Ala Ala Gln Ser Pro Leu Glu Trp Thr Gly
                165                 170                 175

Thr Gln Asp Asp Tyr Leu Ser Val Asp Glu Gln Tyr Phe Asn Phe Ile
            180                 185                 190

Thr Ile Glu Asn Asn Ile Pro Ile Asn Ile Leu Arg Thr Gly Asp Asn
        195                 200                 205

Phe His Ser Gly Ile Tyr Glu Phe Lys Ser Lys Pro Cys Lys Leu Thr
    210                 215                 220

Leu Ser Tyr Gln Ser Thr Arg Cys Leu Gly Leu Pro Pro Leu Cys Lys
225                 230                 235                 240


<210> SEQ ID NO 31
<211> LENGTH: 240
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 31

Arg Met Val His Ile Asn Gln Ala Asp Thr Asp Glu Tyr Leu Ile Phe
1               5                   10                  15

Asn Ala Gly Arg Thr Thr Asp Thr Lys Thr His Gln Gln Lys Leu Asn
            20                  25                  30
```

-continued

```
Leu Glu Phe Phe Val Tyr Asp Asp Phe His Gln Gln Val Met Thr Pro
        35                  40                  45

Trp Tyr Ile Val Asp Ser Asn Ala Trp Gly Val Trp Met Ser Pro Lys
    50                  55                  60

Asp Phe Gln Gln Met Lys Thr Leu Cys Ser Glu Ile Ser Leu Val Thr
65                  70                  75                  80

Leu Glu Gln Glu Ile Asp Asn Val Thr Ile Lys Thr Val Thr Glu Thr
                85                  90                  95

Asn Gln Gly Asn Ala Ser Thr Lys Gln Phe Asn Asn Asp Leu Thr Ala
            100                 105                 110

Ser Leu Gln Val Ala Leu Asp Thr Asn Asn Ile Leu Pro Tyr Thr Pro
        115                 120                 125

Ala Ala Pro Leu Gly Glu Thr Leu Gly Phe Val Pro Trp Arg Ala Thr
    130                 135                 140

Lys Pro Thr Gln Tyr Arg Tyr Tyr His Pro Cys Tyr Ile Tyr Asn Arg
145                 150                 155                 160

Tyr Pro Asn Ile Gln Lys Val Ala Thr Glu Thr Leu Thr Trp Asp Ala
                165                 170                 175

Val Gln Asp Asp Tyr Leu Ser Val Asp Glu Gln Tyr Phe Asn Phe Ile
            180                 185                 190

Thr Ile Glu Asn Asn Ile Pro Ile Asn Ile Leu Arg Thr Gly Asp Asn
        195                 200                 205

Phe His Thr Gly Leu Tyr Glu Phe Asn Ser Lys Pro Cys Lys Leu Thr
    210                 215                 220

Leu Ser Tyr Gln Ser Thr Arg Cys Leu Gly Leu Pro Pro Leu Cys Lys
225                 230                 235                 240


<210> SEQ ID NO 32
<211> LENGTH: 13
<212> TYPE: PRT
<213> ORGANISM: Aleutian mink disease virus

<400> SEQUENCE: 32

Lys Met Gly Ser Glu Gln Leu Glu Trp Gln Gly Ile Gln
1               5                   10
```

USE OF BIRTHING MANURE TO SCREEN FOR PATHOGENIC INFECTION IN FARMED ANIMALS

This application hereby claims the benefit of U.S. Provisional Applications Nos. 61/274,828 and 61/274,829 filed on Aug. 21, 2009 and U.S. Provisional Application No. 61/286,885 filed on Dec. 16, 2009.

SEQUENCE LISTING

This application contains a Sequence Listing that has been submitted via EFS-Web and is hereby incorporated by reference in its entirety. The ASCII copy, created on Dec. 15, 2009, is named 3201-200.txt, and is 53,851 bytes in size.

I. BACKGROUND OF THE INVENTION

A. Field of the Invention

The present invention provides a method to identify and remove pathogen infected animals from a group/herd to prevent the spread of infection and preserve the health of the animals. In particular, PCR screening, utilizing primers appropriate to the pathogen, of both the animals and their environs unambiguously identifies active infections.

B. Description of Problem and Prior Art

Pathogens that infect farmed animals affect both the health and survival of the animals as well as the income of the farmers who raise the animals. For many pathogens, antibiotics are administered to the animals on an intermittent or continuing basis. However, the presence of the antibiotics or their by-products in consumable food products has raised concern about their long-term effect on human and animal health. Immunization against some pathogens is another possible approach, but vaccines for many animal diseases are either not available or are not cost effective. Yet, for other pathogenic organisms no antibiotic or vaccine treatment is available. Early detection of the infection and elimination/removal of the infected animals is the only method that can be used. However, serologic detection methods vary in their sensitivity especially during the early days of infection and may only detect an infection after the animal has started to make antibodies to the pathogen and may, itself, already be infectious.

One pathogen for which there is no effective treatment and no available vaccine is the pathogenic mink Aleutian Disease Virus (mADV). This virus was first described in 1956. All mink Aleutian Disease Viruses are single stranded DNA viruses of the parvovirus family. There are many strains of the virus, but only one known non-pathogenic strain (strain G) while the others are typically fatal. The pathogenic viral strains are absolutely devastating to mink farmers spreading quickly through mink colonies and contaminating the farm site through contact with the mink and their urine and feces. These viruses typically elicit a hyperimmune response in the mink with lethality arising from macro immuno-antigen complexes. The hypergammaglobulinemia condition inflames circulatory filtering organs such as the kidneys (glomerulonephropathy), spleen, and liver causing failure of these organs and death from the complications.

Attempts to find treatments for parvovirus infections have been reported. Alvarez et al. in U.S. Pat. No. 5,785,974 suggests that an immunogenic peptide in conjunction with other immunogenic complexes can be used to make a vaccine that can protect dogs, cats, pigs, and minks. However, the vaccines are proposed to be useful only against another parvovirus infection in mink, Mink Virus Enteritis (MVE) not the Mink Aleutian Disease Virus (mADV). Barney et al. In U.S. Pat. No. 6,054,265 describe peptides that can be used both for screening for certain viruses and for possible treatment. Among other viruses are listed the Mink Virus Enteritis (MVE) and the Aleutian Mink Virus (strain G). The patent basically deals with HIV identification and possible treatment methods are suggested for clinical treatment of infected patients. No direct application to infection with the deadly form of the Aleutian mink virus is discussed. Elford et al. In U.S. Pat. No. 6,248,782 teach that polyhydroxy benzoic acid derivatives are useful in the treatment of diseases caused by retroviruses as well as in the treatment of diseases caused by DNA parvoviruses. No specific example of treatment for mink Aleutian disease is given. As far as is known, none of the above suggested approaches to containing a fatal mink Aleutian disease outbreak has been successfully employed.

The inventive methods disclosed in this patent document are exemplified by the detection and eradication of pathogenic mink Aleutian disease virus from a farmed mammalian herd.

However, the methodological approach taught here is applicable to detecting and eradicating pathogens from any farmed mammalian herd.

II. DESCRIPTION OF THE FIGURES

FIG. 3 is the contiguous partial sequence corresponding to the Stahl mADV strain starting at approximately 272 bp and ending at approximately 4440 bp of the G strain (SEQ ID NO: 17).

FIG. 4 shows the DNA sequence of the ADV G-strain (SEQ ID NO: 18) alongside the contiguous partial DNA sequence of the Stahl mADV strain (SEQ ID NO: 19) so far determined. The alignment was obtained using Clustal W alignment utility located at http:///www.ch.embnet.org/software/ClustalW.html. Primers that worked are shaded while primers that did not work are underlined. The hypervariable region is underlined and identified.

FIG. 5A is the amino acid sequence (SEQ ID NO: 20) of one protein specified by the Stahl mADV that does not include the hypervariable region. This protein is found at the same region of the genome as a protein found in the G strain.

FIG. 5B is the amino acid sequence (SEQ ID NO: 21) of a second protein specified by the Stahl mADV that does include the hypervariable region. This protein is found at the same region of the genome as a protein found in the G strain.

FIG. 6 is a comparison of the partial amino acid sequences of several known mink Aleutian disease viruses aligned (SEQ ID NOS 22-31, respectively, in order of appearance). The hypervariable region is boxed (boxed sequence in StahlX1 disclosed as SEQ ID NO: 32).

Figure 7A:
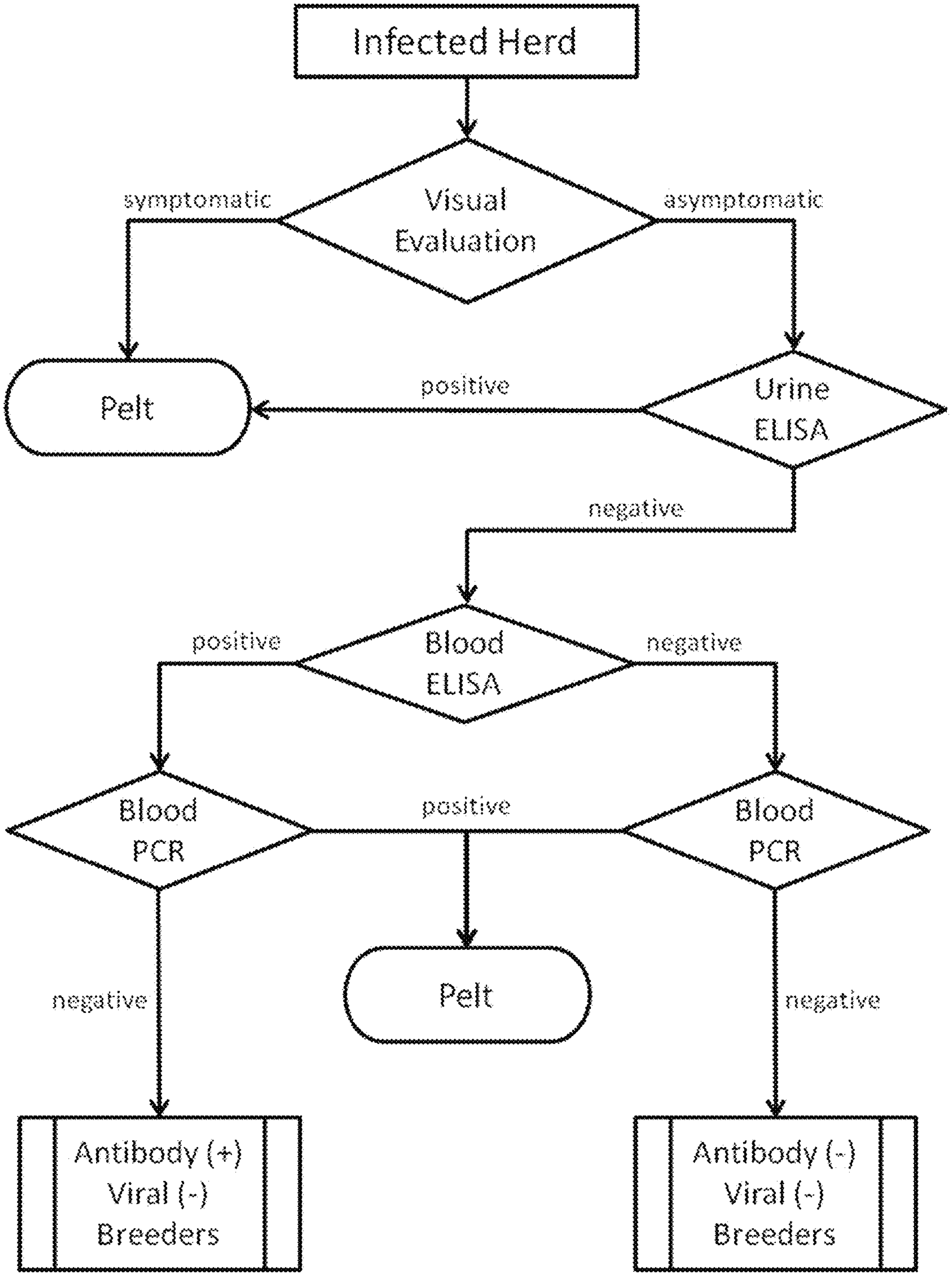

FIG. 7A is an outline of the screening method of the invention indicating the type of test applied at each stage and the disposition of animals that tested positive and negative.

Figure 7B:
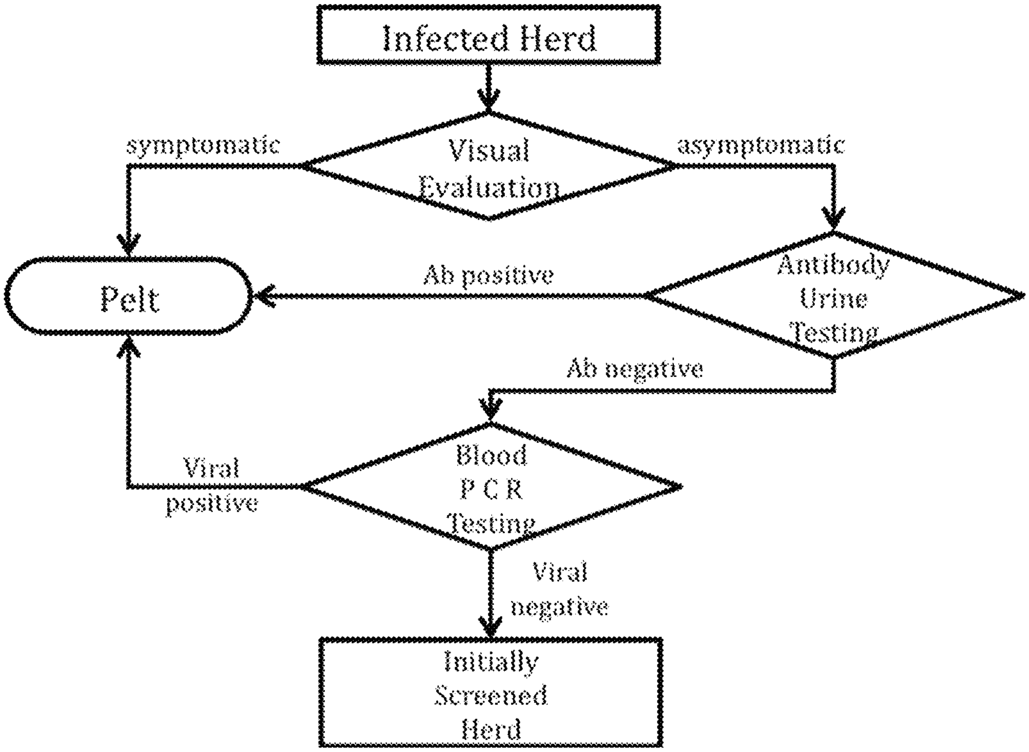

FIG. 7B is an outline of an embodiment of the screening method of the invention in which PCR mADV screening, but not antibody detection, in blood is used.

Figure 7C:
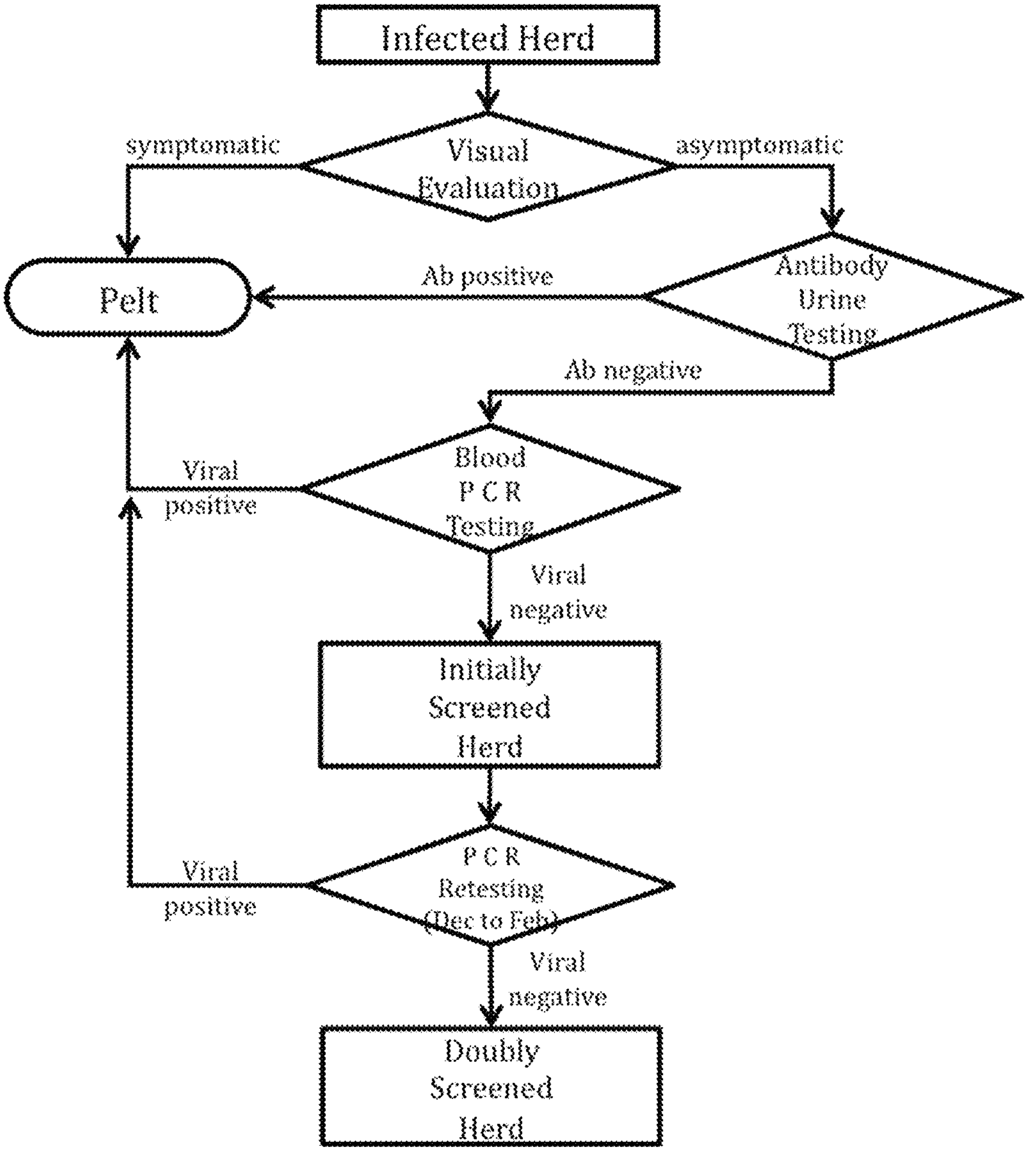

FIG. 7C is an outline of a preferred embodiment of the screening method of the invention in which the herd is retested by PCR screening during the period roughly from December to February.

Figure 7D:
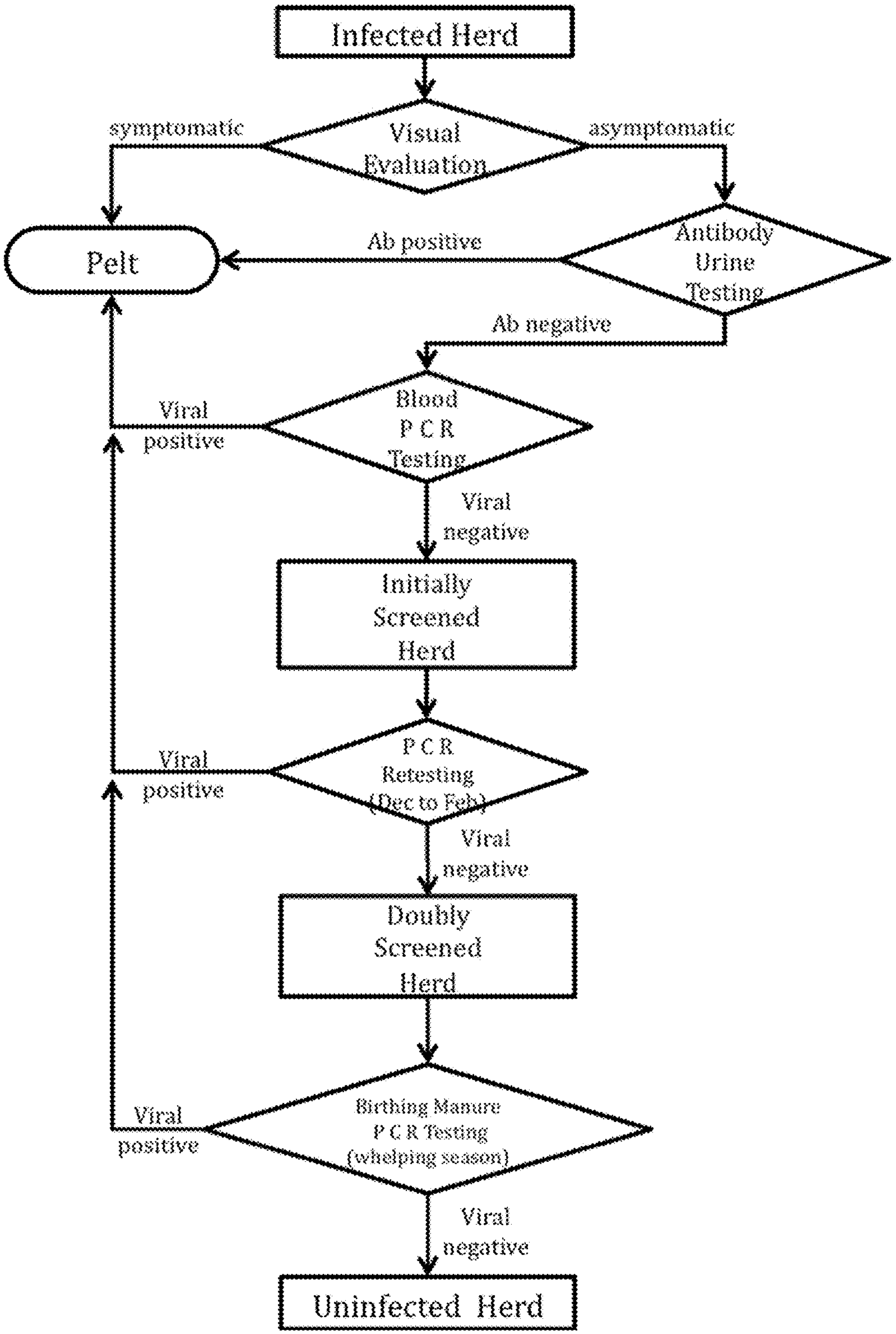

FIG. 7D is an outline of a preferred embodiment of the screening method of the invention in which additional PCR testing of fecal material is performed at the time of whelping.

Figure 7E:
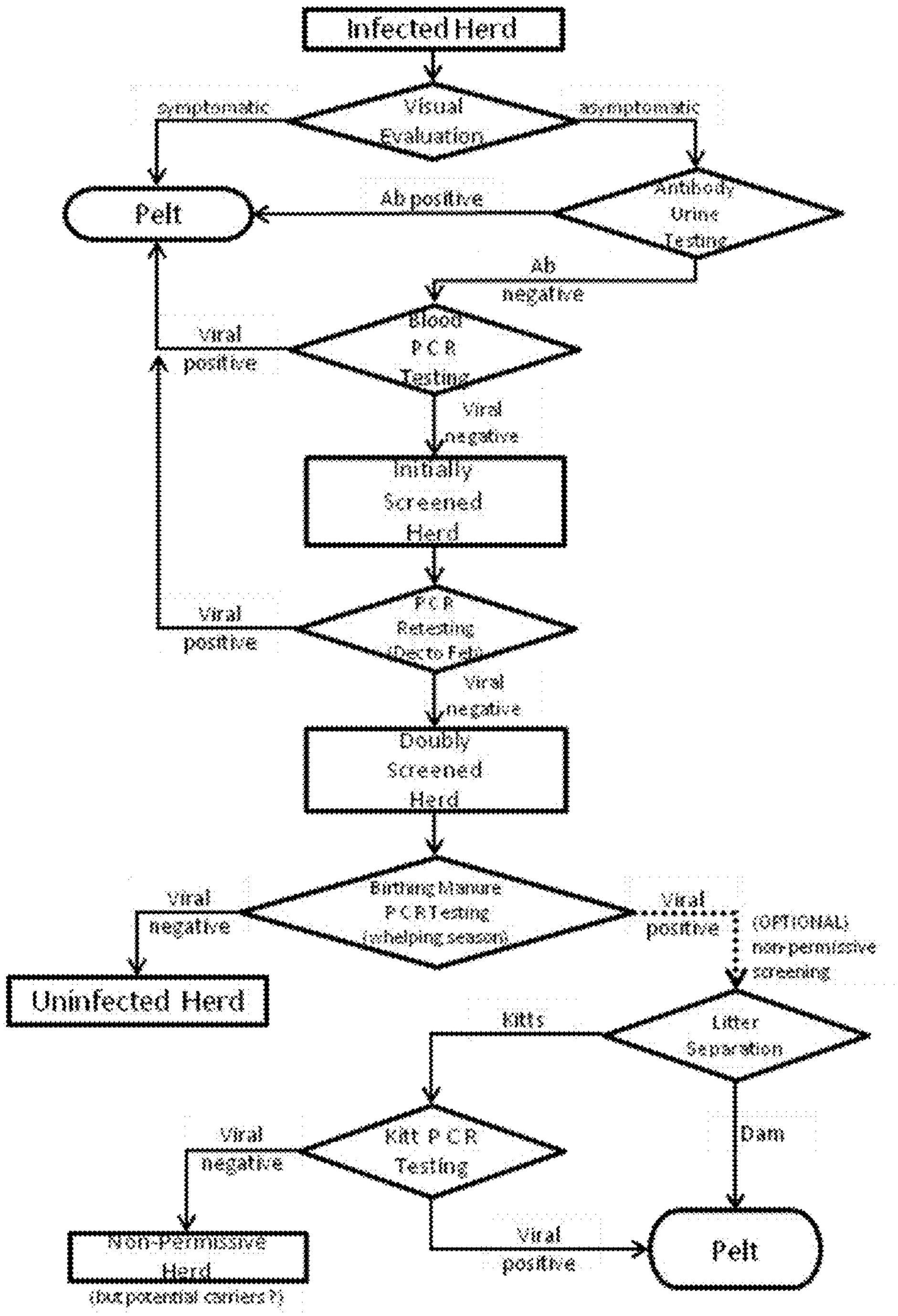

FIG. 7E is an outline of a possible method to identify and place non-permissive animals into a breeding herd.

Figure 8A:
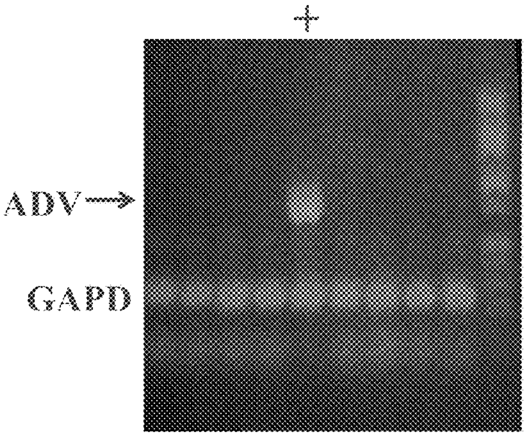

FIG. 8A is a photograph of an electrophoresis gel showing the result of a composite placental manure PCR identification of mADV infection.

Figure 8B:
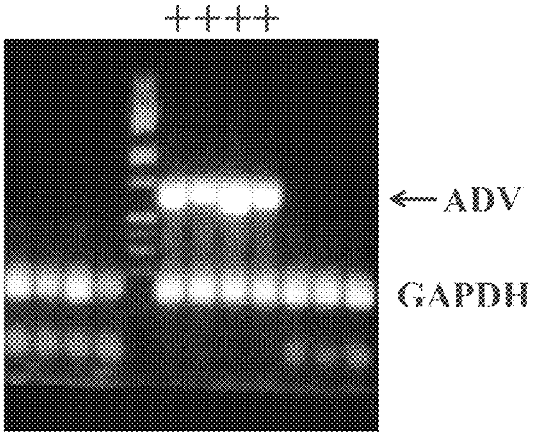

FIG. 8B is a photograph of an electrophoresis gel showing on the left the result of PCR screening of the four females from the composite placental manure sample of FIG. 8A. None are mADV positive. The offspring of three of the four females were all mADV negative. On the right of FIG. 8B is the result of PCR screening of the 7 offspring of the fourth female from the composite placental manure sample of FIG. 8A. PCR identified three of the seven offspring as mADV negative while four of the seven offspring were PCR positive for mADV.

Figure 9:
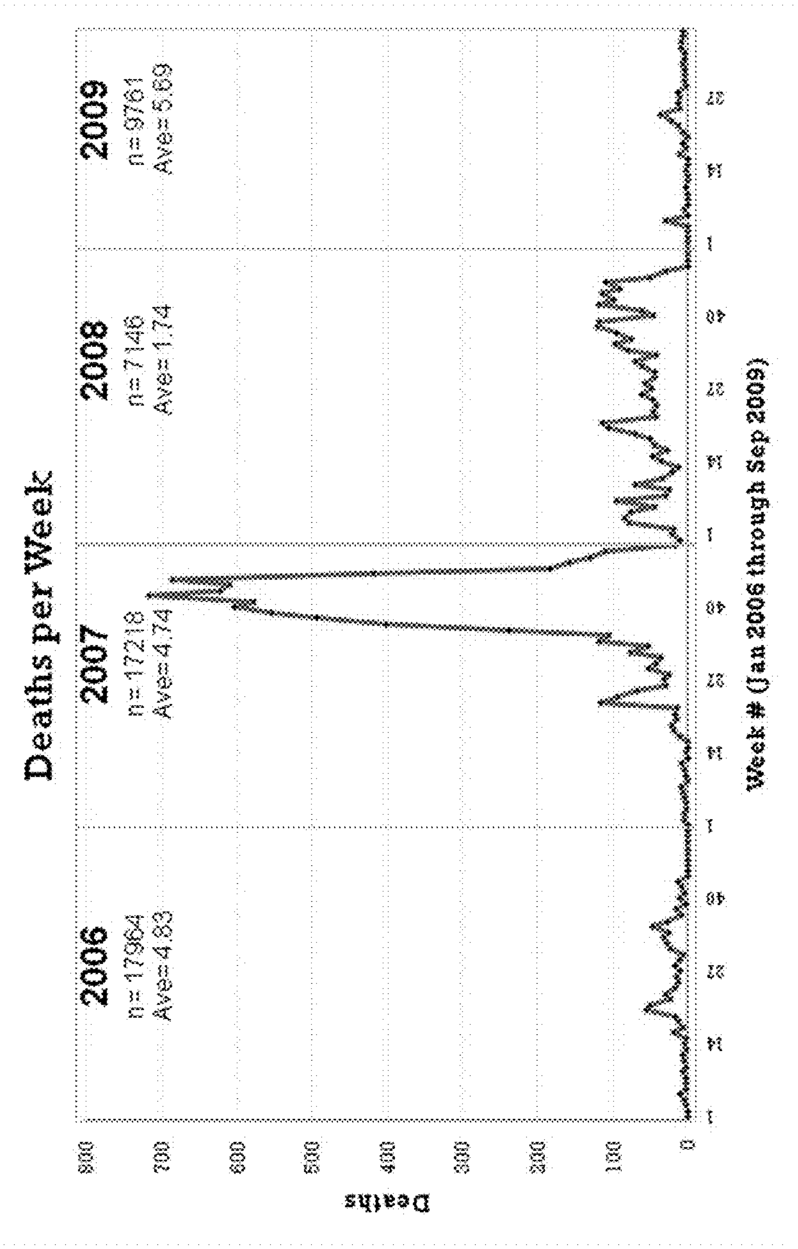

FIG. 9 shows the number of mink deaths per week on a Pennsylvania farm infected with Aleutian mink disease for the years 2006 through September 2009.

III. DETAILED DESCRIPTION OF THE INVENTION

Figure 1:
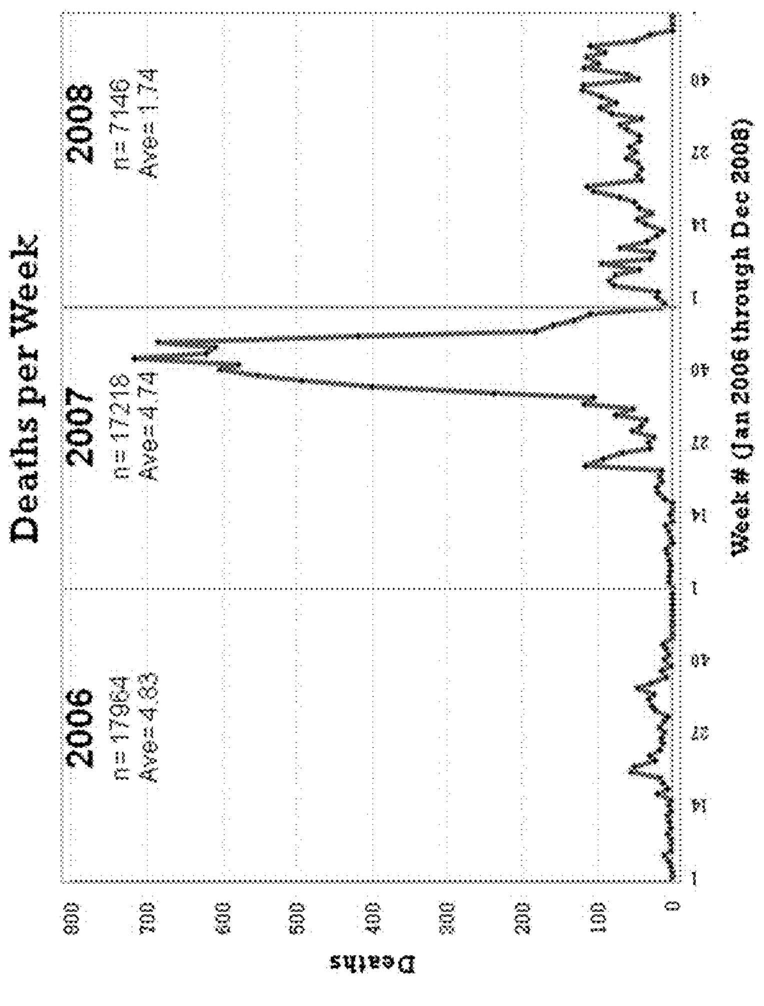
FIG. 1 shows the number of mink deaths per week on a Pennsylvania farm infected with Aleutian mink disease for the years 2006 through December 2008.

A. Characterization of a Rampant Epidemic Infection and Need for a Solution:

The consequences of mADV infection, both in terms of animal survival and of economic survival of the farmer, are extreme and a solution to the problem is urgently needed. Just how extreme the consequences are is highlighted by the experience of the inventors. As noted above, deadly mink Aleutian Disease Virus (mADV) infection can quickly spread through a herd with devastating consequences. FIG. 1 shows the number of mink deaths per week on a Pennsylvania mink farm run by the inventors that had previously been virus free. Prior to June 2006 relatively few deaths occurred generally arising from environmental stress on the herd. Each lineage of minks had been raised on the farm for at least 35 years. In May 2007 health problems in the herd were first noted with some animals having bleeding gums and blood infused water cups. *E. coli* was ruled out and mink ADV was considered a remote possibility since the farm had been mADV free since a mild strain was eliminated by standard husbandry techniques alone in the late 1960's. However, CIEP (counterimmunoelectrophoresis) testing on Jun. 12, 2007 indicted that approximately 30% of barren females were mADV positive.

Despite an extensive testing and animal segregation program using a blood antibody detection procedure (LFIA dipstick—Scintilla Development, Bath, Pa.) the infection continued to spread. Emptied pens that had contained positive animals were disinfected with Kennel Care, reportedly a broad spectrum parvocide. However, animals later transferred to these pens had a 90% reinfection rate, and it was concluded that this parvocide was not effective against mADV. By the end of September and the beginning of November, 2007 approximately 130-150 animals were dying per day as illustrated in FIG. 1. By the end of 2007, the herd had been reduced from roughly 14,000 members and 3,000 breeders to 7,000. At lest 50% of the mink died, another 30% were symptomatic, while 15-20% appeared asymptomatic. The disease spread was unstoppable.

One choice for the 2008 raising season was to dispose of all the animals and start the herd with imported healthy animals. However, this would have meant losing decades of selective breeding and a unique gene pool. In addition, important value would be gained by keeping the naturally resistant mink that survived the epidemic. Realizing the inadequacy of the testing methods, for the 2008 season only 3,000 asymptomatic female breeders were kept with no further testing. However, 1,000 of the 3,000 animals were lost by March, 2008 and about half of the remaining 2,000 females never produced surviving offspring. Of the other 1,000 females, 600 produced diminished litters of 3 or less and 400 produced litters of 4 or more. These 400 animals and their litters were kept but those that subsequently became symptomatic were removed. By late July 2008 it was obvious that an accurate method of virus detection was urgently needed.

B. Development of PCR Based Virus Identification:

The problem for herd management with known antibody testing methods is that the tests detect antibodies produced only after the animal has mounted an immune response some significant amount of time after infection. In addition, the virus persists outside of the animals. Three tests had been in common use in herd management. IAT (iodine agglutination test) is non-specific for mADV and detects only 16-65% of positive CIEP reactors. It is not possible to eliminate mADV from the herd by culling with this test (Gorham, Henson et al., *Infection* [1976] pp 135-158). CIEP sensitivity is uncertain below antigen titers of 8-16. However, a false negative window exists for at least one week post-infection, and CIEP will not determine if the virus was eliminated from the host. The best results for CIEP (0.5-3.2% positive reactors) were determined 1 year post test. (Cho, Greenfield, *J Clinical Microbiology,* January [1978] pp 18-22). If time and resources are available, post exposure antibodies can be detected at a fairly early stage using an ELISA assay (enzyme linked immunosorbent assay). Under farm conditions where a large number of animals (hundreds to thousands) need to be screened, a LFIA strip (lateral flow immunoassay) may be used in place of ELISA. Finally, ELISA is consistently more sensitive than CIEP (95% vs. 65% or less) (el-Ganayni, *Pub Med,* [1992] pp 134-151) and is a rapid cost-effective method of detecting exposure to mADV. However, there exists a false negative window for three weeks post-infection. Further, the false negative rate experienced with LFIA can range from 4-14%. The test will not determine if the virus was eliminated from the host.

If possible to implement, clearly the best alternative available would be testing the animals for the presence of the nucleic acid of the mADV virus using Polymerase Chain Reaction (PCR). PCR can detect virus days after infection and at a very low level (less than 1 femtogram—about 10 genomes of ADV DNA in 2.5 μL of serum (Durrant, Bloom et al., *J Virology,* February [1996] pp 852-861)). There is the possibility of false negatives due to sequestration of the virus, and, for this reason, the test will not determine if the virus was eliminated from the host. However, the ability to unambiguously detect the presence of the virus makes PCR the best choice for monitoring a herd and eliminating the viral infection.

Unfortunately, as of approximately July 2008 no laboratory was immediately available to perform a PCR test for mADV particularly on the scale required (several thousand animals) and at a non-prohibitive cost. Further, most importantly, at that time it was unknown whether a PCR test existed that could detect the strain of mADV infecting the inventors' herd.

(1) Discovery of Appropriate Primers:

In order to develop primers suitable for PCR testing of the infectious mADV, the nucleotide sequence of the non-pathogenic Aleutian mink virus G strain was examined. This sequence had been published by Bloom. The nucleotide sequence was obtained from PubMed.com (NCBI Reference Sequence NC_001662.1). In addition, primers to a universal target, mink glyceraldehyde 3-phosphate dehydrogenase (mGAPDH), were developed. The mGAPDH nucleotide partial sequence (Gram-Nielsen, et al.) was obtained from PubMed.com (GenBank: AF076283.1). Multiplex PCR utilizes more than one set of PCR primers in the same reaction to allow simultaneous amplification of more than one target sequence. In such a controlled reaction, one pair of the multiplex PCR primers is used to detect the presence of the target in question while the other primer pair acts as an internal control to a universal target and assures that the quality of DNA extracted and PCR condition/technique is successfully implemented. Multiplex PCR was used for all testing for the mADV.

The entire G strain sequence was entered into PrimerQuest (Integrated DNA Technologies, idtDNA.com), and possible primers identified following suggestions by the Integrated DNA Technologies' on-line IDT SciTools application. Approximately 50 different primer pairs were suggested. A best guess was made for the first primer pair to be made based on a judgment of what might work. Other primer pairs were tried over a course of about ten months in order to both identify the best primers to use to detect mADV and to identify primers having a sufficient coverage over the genome in order to sequence the entire virus genome. As is well known, primer selection is still an art and not an exact science and much trial and error was involved in determining useful primers. Some of the primer pairs worked while others did not, possibly due to mutual inhibition or to the inability of a particular region to anneal well. Primer pairs were suggested by PrimerQuest based on "relative abilities" to work as a primer based on the input sequence (or partial sequence). The remaining portions of the G-sequence were entered this way to find primers in the remaining untried regions. The oligonucleotide primers themselves were obtained from Integrated DNA Technologies. The DNA extraction conditions for PCR utilized by the inventors are set forth in Appendix "A". The PCR reaction conditions utilized by the inventors are set forth in Appendix "B".

Table 1 lists several of the primer pairs generated, tested, and used in mapping and diagnostic screening based on the G-strain sequence. Those with amplicon sizes listed indicate that the pair worked well. As shown below, five of the primer pairs that were tried and expected to work have zero size indicating the pair did not work. The start and end positions numbers referenced correspond to the G strain sequence positions.

TABLE 1

| Primer (For/Rev) | Amplicon Size (bp) | Start (bp position) | End (bp position) | Conserved Match (forward) | Conserved Match (reverse) |
|---|---|---|---|---|---|
| V1/V0 | 0 | 18 | 381 | ?/24 | 23/24 |
| V1/V1 | 0 | 18 | 932 | ?/24 | 23/24 |
| V1a/V1a | 954 | 273 | 1227 | ?/24 | 23/24 |
| V2/V2 | 934 | 895 | 1829 | 24/24 | 21/24 |
| V3/V2 | 378 | 1451 | 1829 | 23/24 | 21/24 |
| V3/V3 | 883 | 1451 | 2334 | 23/24 | 24/24 |
| V4/V4 | 981 | 2064 | 3045 | 23/24 | 24/24 |
| V4a/V5a | 0 | 2356 | 3325 | 23/24 | 21/24 |
| V4b/V5b | 999 | 2525 | 3524 | 24/24 | 24/24 |
| V5/V5 | 802 | 3022 | 3824 | 24/24 | 24/24 |
| V6/V6 | 0 | 3742 | 4766 | 21/24 | ?/24 |
| V6a/V6a | 881 | 3559 | 4440 | 23/24 | ?/28 |
| V7/V6 | 0 | 4223 | 4766 | 25/26 | ?/24 |

tried and the primers were ordered. Astoundingly, the first primer pair attempted, V3-F/V2R worked and yielded an amplicon of ~378 bp. Because this amplicon size was too close to the GAPDH amplicon size to clearly resolve on the electrophoresis gel, another primer pair, V3-F/V3-R, was tried, and it also worked and yielded a large amplicon easily distinguished from GAPDH. Shortly after this success, primers that span the hypervariable region (which was previously known by Bloom) were sought in order to identify the particular mADV strain infecting the herd.

Once primers were identified that covered the hypervariable region, the sequence of the hypervariable region was obtained. It was quickly realized that the mADV strain on the inventors' farm did not correspond to any strain in the published literature and was, therefore, a novel strain. The sequence of the Stahl mADV genome was determined as indicated below in Section B (2). Subsequent to the initial identification of the first primer pairs, portions of the G strain sequence were entered into PrimerQuest and possible primers suggested. Selection of several primer pairs were The oligonucleotide sequences of some of the above primers used include:

```
V1a:
                                        (SEQ ID NO: 1)
5' - TTA ACG ACG GTG AAG GAG TTG CCT - 3' (forward)

                                        (SEQ ID NO: 2)
5' - TCT TCT GGA GTA AAG CAA CCA ACG - 3' (reverse)

V2:
                                        (SEQ ID NO: 3)
5' - TGG TTA CTT TGC TGC TGG TAA CGG - 3' (forward)

                                        (SEQ ID NO: 4)
5' - TCC TCT GTT TAA GTG GCT CTG CGT - 3' (reverse)

V3:
                                        (SEQ ID NO: 5)
5' - ACC ATC CTA ACC AAG CAA GGT GGA - 3' (forward)
```

-continued

```
                                   (SEQ ID NO: 6)
5' - ACA CGT GTC TTG GAG CAC TTC TCT - 3' (reverse)

V4:
                                   (SEQ ID NO: 7)
5' - TGC CAC AAC TGC CAC GAA GAA TAC - 3' (forward)

                                   (SEQ ID NO: 8)
5' - ATT GGG TTG GTT TGG TTG CTC TCC - 3' (reverse)

V4b/V5b:
                                   (SEQ ID NO: 9)
5' - CAG CAC TGG CGG CTT TAA TAA CAC - 3' (forward)

                                  (SEQ ID NO: 10)
5' - ACT ACC CTG TAA CCC TGC TGG TAT - 3' (reverse)

V5:
                                  (SEQ ID NO: 11)
5' - GGA GAG CAA CCA AAC CAA CCC AAT - 3' (forward)

                                  (SEQ ID NO: 12)
5' - TTC AAA GTG TGT GCC TGA AGC AGC - 3' (reverse)

V6a:
                                  (SEQ ID NO: 13)
5' - CAA CCA AAG GTG CAG GTA CAC ACA - 3' (forward)

                                  (SEQ ID NO: 14)
5' - GGA AGT ACA CAG TAT TTA GGT TGT TCA C - 3'

(reverse)
```

The primer pair used for mGAPDH is:

```
                                  (SEQ ID NO: 15)
5'- AAC ATC ATC CCT GCT TCC ACT GGT - 3' (forward)

                                  (SEQ ID NO: 16)
5' - TGT TGA AGTCGC AGG AGA CAA CCT- 3' (reverse)
```

Figure 2:
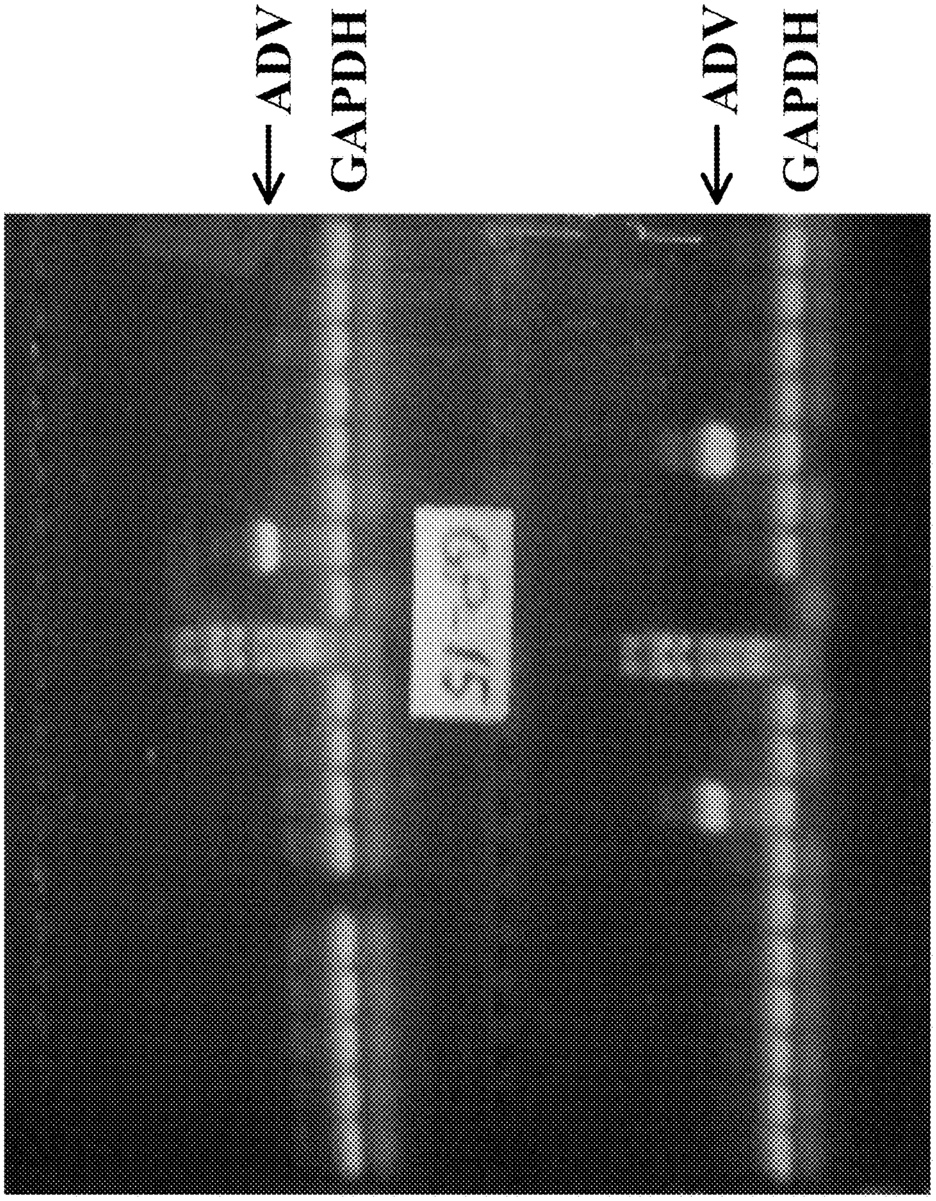
FIG. 2 is a photograph of a typical electrophoresis gel showing the locations of the GAPDH and mADV marker amplicons.

As noted above, an initial attempt at diagnosing the presence of mADV via PCR utilizing primer V3 forward paired with V2 reverse yielded an amplicon of 378 bp. The size of this amplicon was too similar to the mGAPDH amplicon of 250 bp to be reliably separated on the electrophoresis gel. Therefore we ultimately chose an alternative mADV primer pair (V5) which would yield a larger amplicon (802 bp). This resolution was sufficient to clearly distinguish the mGAPDH and mADV amplicons. FIG. 2 is a photograph of a typical electrophoresis get and shows that the GAPDH and mADV amplicons are well resolved and separated. In addition, the V5 primers spanned the hypervariable region of the mADV (Bloom, et al.). This not only yielded an amplicon distinguishable from the mGAPDH amplicon, but also enables the strain typing of the viruses by subsequent sequencing of this amplicon from different viruses The V5 primer pair represents the preferred enablement and is used routinely as the diagnostic screening tool of choice for mADV.

As will be readily evident to those skilled in the art, in addition to the primer pair sequences listed above, the reverse complement sequences of the above forward primers could also work as reverse primers (i.e. reverse complement of V5 forward equals V4 reverse). Similarly the reverse complement sequences of the above reverse primers could also work as forward primers (i.e. reverse compliment of V4 reverse equals V5 forward). (This is easily seen illustrated in FIG. 4.) In both these examples, a new primer companion would have to be selected because the direction of amplification would now be different. All primers disclosed should also function properly if at least approximately 85% of the bases are identical to the primer sequences identified and appropriately matched with a primer pair under slightly different annealing temperatures. As is evident to those skilled in the art, the disclosed primers should also function properly if 1 or more bases were added to the 5'-end and 1 or more bases truncated from 3'-end and similarly when 1 or more bases were added to the 3'-end and 1 or more bases truncated from 5'-end (when referenced to the G-strain sequence). In addition, as will also be readily evident to those skilled in the art, any nested primers, being a subset of the target region of the described primers, are included in the scope of this disclosure as are other primer pairs that overlap or are immediately adjacent to the primers described in detail above.

(2) Sequencing of Mink Aleutian Disease Virus:

A novel mADV strain has been identified based on DNA sequences obtained from mADV amplicons produced from the PCR reactions using the above selected primers. Amplicons were sent to GeneWiz (GeneWiz, Inc., South Plainfield, N.J.) for DNA sequencing. Overlapping DNA segments were assembled using DNA Baser software (dnabaser.com) to form a contiguous sequence. This sequence was compared to the only published full-length sequence G-strain mADV (Bloom, et al.) obtained from PubMed.com (NCBI Reference Sequence: NC_001662.1) by the use of Clustal W software (npsa-pbil.ibcp.fr) and determined to be a contiguous partial sequence that starts relatively around 272 bp and ends around 4440 bp out of the 4801 bp total.

Table 2 illustrates the relative alignment positions and sizes of the mADV amplicons used to sequence the mADV genome in relation to the G-sequence (vertical bars). Progression over time is indicated from top to bottom starting with V3/V2 and ending with V7/V7. Hatched trellis regions indicate the part of the mADV DNA sequence obtained using the different primer pairs. Region 2.8 kb (horizontal bars along the top of the table) indicates the relative hypervariable region (3096-3134 bp). The assembled mADV contiguous region is depicted in the bottom row and was obtained from overlapping DNA sequences (273-4440 bp). It was assembled without any gaps by the use of the overlapping amplicons designed by proper primer pair placements. This is considered a partial sequence in relationship to the entire G-sequence since approximately the first 272 bp at the 5' end and 361 bp at the 3' end have not yet been identified.

TABLE 2

| G-seq (kb) | 0.001 | 0.4 | 0.8 | 1.2 | 1.6 | 2.0 | 2.4 | 2.8 | 3.2 | 3.6 | 4.0 | 4.4 | 4.8 |
|---|---|---|---|---|---|---|---|---|---|---|---|---|---|
| G-seq | | | | | | | 1-4801 bp | | | | | | |
| V3/V2 | | | | | 378 bp | | | | | | | | |
| V3/V3 | | | | | 883 bp | | | | | | | | |
| V5/V5 | | | | | | | | | 802 bp | | | | |
| V1/V1 | | | | | | | | | | | | | |
| V4/V4 | | | | | | | 981 bp | | | | | | |
| V2/V2 | | | | 934 bp | | | | | | | | | |
| V6/V6 | | | | | | | | | | | | | |
| V4a/V5a | | | | | | | | | | | | | |
| V6a/V6a | | | | | | | | | | 881 bp | | | |
| V1a/V1a | | | 954 bp | | | | | | | | | | |
| V4b/V5b | | | | | | | | 999 bp | | | | | |
| V0/V0 | | | | | | | | | | | | | |
| V7/V7 | | | | | | | | | | | | | |
| contig | | | | | | | 273-4440 bp | | | | | | |

The primer pairs that span the hypervariable region are V5-F/V5-R and V4b-F/V5b-R. The contiguous partial sequence of the Stahl mADV strain is presented in FIG. 3. While the standard procedure of starting the numbering sequence at "1" has been utilized in FIG. 3, as noted above, the Stahl mADV sequence is a contiguous partial sequence starting about 272 bp in from the start of the G strain sequence.

A comparison of the nucleotide sequences of the G-strain and the Stahl strain is shown in FIG. 4. The alignment information shown in FIG. 4 was generated using the Clustal W alignment utility located at http://www.ch.embnet.org/software/ClustalW.html. The strain identifications, numbers, and primer designated sites have been added to the Clustal W comparison. The primers that worked are shaded, while the primers that did not work are underlined. The hypervariable region starting at 3096 (G-strain reference) is labeled and underlined. The mADV contiguous sequence was BLAST searched against all other published sequences and no other identical match found (PubMed.com). The mADV sequence shown in FIGS. 3 and 4 is the first time identification of the sequence of the highly infectious mADV virus has been determined. In particular, it will be appreciated by those skilled in the art that any primer pair that spans the hypervariable region falling within the V5 primer pair including the nucleotide sequence of the hypervariable region disclosed in this patent document will generate a PCR amplicon specific to the Stahl mADV strain. Further, since the hypervariable region specifies the strain type, use of such a primer pair that spans the hypervariable region with other ADV strains will permit an accurate strain typing that can be used to not only identify the strain but also to trace infections from place to place, herd to herd.

Thus, while other methods of performing PCR have been developed (such as rapid PCR techniques using fluorescence resonance energy transfer probes) that do not rely on electrophoresis gel determinations, any such technique that relies on the amplification or identification of the sequences disclosed in this patent document is considered to be encompassed by the present disclosure.

FIG. 5 shows the amino acid sequence of two proteins predicted from the partial nucleotide sequence determined for mADV. FIG. 5A shows the amino acid sequence of one protein specified by the Stahl mADV that does not include the hypervariable region. This protein is found at the same region of the genome as a protein found in the G-strain. FIG. 5B shows the amino acid sequence of a second protein specified by the Stahl mADV that does include the hypervariable region. This protein is found at the same region of the genome as a protein found in the G-strain. The sequences were generated using the ExPASy Proteomics Server, Swiss Institute of Bioinformatics (http://www.expasy.ch/tools/dna.html). FIG. 6 is a comparison over a limited span of the amino acid sequences of several mink viruses including the G-strain and the Stahl strain. To generate FIG. 6, a nucleotide BLAST search was conducted using the Stahl strain nucleotide sequence as the query on PubMed.com (http://blast.ncbi.nlm.nih.gov). Several similar DNA sequences obtained were selected for translation using ExPASy. The resulting amino acid sequences were then aligned using a CLUSTAL W protein alignment utility (http://npsa-pbil.ibcp.fr/cgi-bin/npsa_automat.pl?page=/NPSA/npsa server.html). The comparative sequences span the hypervariable region (indicated by the box). The amino acid sequence of the Stahl strain clearly differs from the others in several locations. Several different single nucleotide polymorphisms (SNP's) were identified within the Stahl strain DNA sequence. The differences in the DNA base at these positions each produce a change in the corresponding coded amino acid. This type of variant is known as nonsynonymous because a different polypeptide is produced. Table 3 shows some SNP's identified by the DNA location and resulting change in coded amino acid.

TABLE 3

| SNP location (bp) | Nucleotide = Amino Acid |
|---|---|
| 301 | T > G = H > Q |
| 412 | A > G = I > M |
| 575 | T > C = F > L |
| 908 | T > A = C > S |
| 1059 | G > C = S > T |
| 1068 | C > T = T > I |
| 1078 | A > C = E > D |

It is unknown at the time of drafting this patent document whether the identified changes are responsible for the virulence of the Stahl strain. There are indications in the literature that other sites along the amino acid chain may also be involved in determining the relative virulence of the viruses.

C. Procedure for Elimination of Pathogens from a Farmed Herd:

In order to eradicate a rampant epidemic infection from a herd, all testing methods available are used. In the case of a mink farm, both an antibody detection method (ELISA or LFIA) and PCR are used. However, even before animal inspection and testing can begin, a virus free clean facility needs to be created so that animals transferred out of the infected herd are not reinfected. Appendix "C" outlines the sanitation procedure used on the farm. Importantly, Oxine solution with and without added detergent has been found to be an effective parvovirus viracide. Before cleaning with any product, care should be taken to ascertain that product will inactivate the infecting pathogen. In particular, environmental PCR testing as described in Appendix "E" should be employed.

Once a clean facility has been obtained, animal selection and testing can begin. FIG. 7 shows in outline form the methodological sequence originally employed to identify and remove infected animals from the herd. Initially a visual examination of the animals is made to observe any animals showing clinical symptomology. Clinical signs such as lethargy, poor appetite, underweight, ventral staining, discharge from the mouth and bleeding gums are all indications but not proof of an infected animal. Considering the consequences of keeping a potentially infected animal in the herd, no consideration at this time on an infected farm is given to the actual clinical cause of the observed condition of the animals. These animals are immediately removed from the herd, and, in the case of mink, are pelted. Only visually asymptomatic animals are considered for testing. Urine samples are obtained from these animals. For mink, urine is collected from a suspended cup placed below the animal and above the manure pile. The urine is tested with an antibody detecting method (ELISA may be used but the use of a LFIA strip provides a quick result and is easily employed in the field). LFIA can only detect antibodies after the 14-21 days it takes for the animal to mount a sufficient immune response. However, a positive urine antibody test (using LFIA) on an asymptomatic animal indicates a prolonged and persistent viral infection and that sufficient renal damage (glomerulonephropathy) has already occurred from antibody/antigen complexes. Healthy animals will not excrete antibodies in urine unless the renal system has deteriorated. The antibody positive animals are removed from the herd, and, in the case of mink, are pelted.

An antibody negative urine animal is now a candidate for further antibody testing of its blood. ELISA or LFIA may be used. Again, as noted above, LFIA is more conveniently used. LFIA testing of blood is a more sensitive test and does not rely on extensive renal damage having occurred. Blood is collected for both antibody testing and PCR testing at the same time according to the method described in Appendix "D". Whether the blood tests positive or negative for antibodies, the blood is still subjected to further PCR testing. In the case of an animal with antibody positive blood, it is possible that the animal has acquired a natural immunity to the virus and should be kept in the herd. If the blood PCR test indicates virus present in the antibody blood positive animal, the animal is removed from the herd. If the blood PCR test indicates no virus present in the antibody blood positive animal, the animal is kept in the herd and identified as antibody (+) virus (−). If the blood PCR tests positive for virus present in the antibody blood negative animal, the animal is removed from the herd. If the blood PCR test indicates no virus present in the antibody blood negative animal, the animal is kept in the herd and identified as antibody (−) virus (−). At this point in the selection process, both the antibody (+) virus (−) and the antibody (−) virus (−) animals are kept in the herd.

After some experience utilizing the above outlined protocol, it was appreciated that nothing was being gained by testing the blood for antibodies. The subsequent PCR test for viral presence is a necessary and sufficient selection criterion. PCR mADV positive blood tests indicate an infected animal and indicate that the animal should be removed from the herd. However, as in the earlier protocol where antibody positive PCR mADV negative animals were not removed from the herd (since the antibody presence probably resulted from the animal naturally mounting a sufficient immune response to the virus) in the revised protocol PCR mADV negative animals are kept in the herd. The preferred protocol embodiment of the invention is outlined in FIG. 7B.

As the animals are characterized and the infected animals removed or destroyed, the healthy animals are transferred to sanitized pens. For this transfer, the animal is caught with Oxine soaked gloves (500 ppm), placed in a small carrier and dowsed repeatedly in a 200 ppm solution of Oxine.

Into this solution is also added a small amount of dish washing soap to aid as a surfactant for the aqueous Oxine solution to penetrate the highly hydrophobic under wool. In this manner, the external surface of the animal is treated as completely as possible with Oxine. Oxine aids in the elimination of environmental virus on the mink. It has been discovered that it is possible to have a viral blood negative mink in a viral positive pen. Swabbing of the tops and bottoms of pens and analysis of the swabs by PCR revealed that the top of the pen was usually more contaminated than the bottom of the pen. In such a pen, a virally negative mink either was not yet infected or the viral load was not yet sufficient to cause an infection, but the virus may be carried on the outside of the body. When a mink from an infected pen is moved into a clean area, it may unknowingly cause a reinfection at a later date. Thus, passing the viral PCR tests is not sufficient to maintain a virus free herd without also sanitizing the exterior of the mink. The 200 ppm Oxine solution was not found to have any effect on the eyes or mucus membranes of the mink and is an effective tool for killing the virus in the mink's coat. Only after undergoing this cleansing methodology was a mink placed into a freshly sanitized, quarantined, windward area of the ranch.

However, it should be appreciated that it is possible that a recently infected animal may not be detected by PCR testing. Accordingly, retesting of the animals using the preferred PCR protocol may be required to either confirm the absence of the virus in the herd or to remove any remaining infected animals. Based on the inventors' experience, it is believed that the optimum windows for testing are December during pelting, late February prior to breeding, and whelping season. PCR retesting according to the protocol set out in FIG. 7C of the mink herd on the inventors' farm two months after the above described testing and selection process discovered that about 1.5% of the females and less than 1% of the males were still infected. In addition, the pens of these animals were resanitized and left dormant. As can be seen in FIG. 9, the viral elimination protocols outlined above substantially reduced the mink mortality for 2009. It should be noted that a variety of causes unrelated to mADV infection result in some level of mink mortality as is reflected in FIG. 9 for 2009. However, it should also be appreciated that the viral elimination protocols and hygienic cleaning of the farm result overall in a much healthier herd.

Another method of monitoring the health of the herd has been discovered using placental manure screening that will be described below.

D. Procedures for Continued Monitoring of an Animal Herd:

In a large farm consisting of potentially many thousands of animals, the cost in time and expense of utilizing the protocols outlined above for eliminating a contagious infection from the herd is a relatively small fraction of the loss attributable to the decimation of the herd population. Once a relatively infection free herd is established, other ongoing monitoring protocols can be utilized.

(1) Placental Manure Sampling:

The females of many mammalian animal species, including mink, soon after giving birth devour the discharged placenta. Malformed or dead offspring may also be consumed. The reason for this behavior is not well understood but may be linked to the need for hormones to reduce uterine bleeding (in mammals). In the case of mink, shortly after consumption of the placenta, the female mink passes a black, tarry, and shiny stool. Typically the stool is found in a far corner of the pen or even on the ground. If deposited relatively soon prior to discovery, the stool is easily sampled by inserting a small diameter tube a fixed distance into the medium to collect a sample size of approximately 35 uL. This sample is placed in a labeled tube for submission for PCR. If the stool has been deposited for some time and the weather conditions are dry, a hard skin begins to form around the medium that must be broken for internal sampling.

Using PCR methods described above to analyze a sample of the stool, it has been discovered that mADV can be detected in animal manure as shown in FIG. 8A. The placental stool PCR mADV screening enables the removal from the herd of the affected dams and litters the day of whelp. Very importantly, this method provides a non-invasive and non-tactile method of screening that does not disrupt the mink during this period with unnecessary handling. In addition, the method minimizes the spread of the disease through contact and handling at the beginning of the spring and summer (the whelping season), the most contagious times of the year. When a positive manure sample is identified, the animals are removed from the herd, and, in the case of mink, euthanized. To reduce the likelihood of the spread of infection, the litters adjacent to the infected litter are removed to pens on the leeward side of the ranch for quarantining and observation as an extra precaution. All empty pens are then cleaned and resanitized as taught previously. Most importantly, since the stool contains material from all the offspring as well as the mother, analysis of the stool by PCR discovers infection in the offspring as well as the mother. Based on the discovery of pathogen detection by PCR in the placental manure of mink, detection of pathogen infection in the placental manure of other species in which the mother consumes the placenta may be accomplished by PCR analysis for a representative pathogen nucleotide sequence.

On a ranch where the virus has been substantially eliminated according to the protocol methods of the present invention, to reduce the number of manure samples to be analyzed by PCR, sampling of composite birth stools from several animals can be used as an economical and rapid method for virus detection. For example, it has been found that composite pooling of samples from four females where one sample is positive for the virus will reveal the entire composite to be positive. (See FIG. 8A.) FIG. 8A shows the results of PCR mADV analysis of 9 different pooled placental manure samples. As shown, the mADV virus was found in one pooled sample. Thus the dilution factor of the sample is not a concern due to the high sensitivity of the PCR method. Higher pooling numbers are possible but the limits have not been explored as of yet. It is very important to record all members of the pooled sample and the location of each of the members for future reference should PCR mADV analysis of individual samples be required. In all cases of a PCR mADV positive composite sample, the individual samples that made up the composite will have to be retested by themselves to find which of the pooled samples had the infection so that the positive animals associated with that sample can removed from the herd. Farms that have a history of the disease may not be able to afford high pool numbers due to the greater probability of positive samples.

Screening during the whelping season of the placental manure of all animals in the Pennsylvania herd after the elimination of infected animals according to the protocol methods of the present invention set forth above yielded some interesting results. Two composite placental manure samples (four dams in each composite) were PCR positive for mADV. As noted above, FIG. 8A shows the screening result for composite samples indicating that one composite sample was PCR positive for mADV. PCR analysis was then applied to samples from each dam and their offspring in the two PCR mADV positive composite pools (not shown). In the first positive composite pool, 3 dams and all of their offspring were PCR negative for mADV. The remaining dam and her offspring were PCR positive for mADV. Clearly, dilution by composite pooling did not affect the accurate PCR detection of mADV. The PCR mADV positive animals were removed from the herd.

PCR mADV analysis of animals in the second positive pool was surprising. The results of the individual screening for these animals is shown in FIG. 8B. FIG. 8B shows the PCR results for all four females (on the left of the central ladder column) and the seven offspring of one female (on the right of the central ladder column). All four females were found to be PCR mADV negative. Three of the four litters (18 offspring) were also PCR negative for mADV (not shown). The fourth PCR mADV negative female had a litter of 7 offspring in which 3 of the 7 were PCR mADV negative while 4 of the 7 were PCR mADV positive as shown on the right of the central ladder column of FIG. 8B. Two very important discoveries come out of this data. First, PCR testing of the placental manure picked up mADV infection in the offspring. Suprisingly, PCR mADV testing also revealed the presence of an otherwise healthy and PCR mADV negative female that carried the mADV virus and was capable of passing the virus on to her offspring. Screening by the composite sampling method permits not only the identification of infected animals that were kept in the herd having passed the initial screening tests, but, most importantly, also permits the identification of carrier animals that need to be removed from the herd in order to eliminate all infection from the herd. It is probable that the PCR mADV negative female animal was "non-permissive"; that is, the virus is unable to infect the animal's cells even though virus particles remain sequestered in the animal. The female apparently passed on her "non-permissive" genome to 3 of her offspring but not the other 4. Prior to this discovery, the relevant literature has taught that the vertical transmission of disease caused by mink disease virus was 100%. The results shown in FIG. 8B clearly indicate otherwise.

This is the first indication that there is some genetic variation in mADV susceptibility occurring between generations, and that there is a genetic basis that makes the animals non-permissive. Clearly, all the fetuses develop simultaneously in utero and are simultaneously exposed to the virus, but the virus does not affect some of the fetuses. Interestingly, antibody testing of the non-permissive dam also did not indicate any antibodies. Based on this example, there is a strong suggestion that a genetic solution to the mADV infection problem may be found. Not only is placental manure screening a cost and time effective way to monitor the health of the herd, it is particularly important as a way to identify non-permissive animals as early as the whelping day so that infected animals can promptly be removed from the herd before there is an opportunity for them to pass on the virus. The full screening protocol setting forth the most preferred embodiment is shown FIG. 7D.

In the future, the inventors intend to try to identify the genetic markers that are responsible for the "non-permissive" characteristic with the hope that, with knowledge of the gene sequence identifying the non-permissive characteristic, a whole herd can be created that is resistant to mADV. Alternatively, the identification of non-permissive animals using PCR for mADV on placental manure samples, also raises the interesting possibility of creating, by breeding, a herd of animals all of which possess a non-permissive genome. At this time it is unknown whether breeding non-permissive animals with other non-permissive animals will produce a stable gene line of non-permissive animals. A possible alternative scenario for establishing a breeding herd of non-permissive animals is set out in FIG. 7E. Instead of pelting the kits that are identified by a PCR mADV positive unpooled manure sample, the kits are individually retested by PCR for mADV. Some of the kits will test positive since they are the source of the positive manure sample. Any PCR mADV negative kits would be segregated and used to establish a non-permissive herd. At this point it would be unknown whether the kits harbor a sequester virus and would transmit the virus to their offspring. Any remaining PCR mADV positive kits as well as the PCR mADV negative dam that is now known to harbor the virus would be pelted. Repetitive identification and segregation of non-permissive animals in subsequent generations should establish a gene line that breeds true for non-permissive animals.

(2) Saliva Sampling:

Finally, for continued monitoring of the herd, an alternative saliva collection process for PCR can also be employed. Saliva can be collected from mink by allowing them to bite upon a thin plastic tube or string or absorbent material such that sufficient saliva is collected. No handling of the animal is required which lessens the transmission of the disease and speeds collection. Typically this sampling is best achieved just prior to feeding time for the animals as they are very aggressive towards objects placed through the wire cage. The chewing process on the tube or string or other material is sufficient to deposit enough saliva for nucleic acid detection. Return visits may be required for animals that are not compliant.

One caution for this method is that the sampling tube or string or other material may not touch the wire cage since environmental virus is likely to be included in the sample. Care must be taken at this point to ensure that no contamination results before the sample is safely placed in its labeled sampling container. As taught before with respect to sample acquisition for antibody testing (LFIA) and PCR testing, the sampling lid is opened and the portion of tube or string or other material is cut off allowing it to fall into the container and then the lid is closed. Specific duties of each hand are practiced as described in Appendix "D".

(3) Demonstration of Elimination of Pathogen From a Herd:

The success of the screening method taught in this patent document can clearly be seen by examination of FIG. 9 which extends the data of FIG. 1 for the year 2009. It is immediately evident beginning in the late fall of 2008 that, after employing the testing and selection method taught in this patent document, the death rate had fallen at least to the levels observed before the mADV outbreak, if not even lower. The reason the death rate is never zero is due to the fact that some deaths naturally occur due to environmental stress and other factors. However, the method taught herein has clearly been successful in eliminating the mADV epidemic.

The method of the present invention has been exemplified by application to the elimination of mADV from a mink herd. The basic principles of screening using PCR detection of a pathogen's nucleic acid signature, with or without additional screening technologies such as antibody testing (ELISA or LFIA) to identify and remove infected animals from a herd has general applicability to a wide range of animals. The techniques may even be extended to populations of wild animals particularly through the PCR testing of manure.

The discovery of primers that can identify the lethal mADV permits the assembly of testing kits that may be employed on mink farms. Simple kits may contain just the primers for mADV with the users supplying reference primers and laboratory facilities. More advanced kits may contain not only the mADV primers but also the GAPDH or other internal reference marker primers along with the remaining materials required to screen by PCR.

Appendix "A"

DNA Extraction

Samples received for detection of mink Aleutian Disease Virus (mADV) were processed using RNase/DNase free microcentrifuge tubes and sterile pipette tips containing aerosol filters. Samples collected consisted of 2mL microcentrifuge tubes containing either:

1. Blood soaked cotton swab
2. Urine soaked cotton swab
3. Environmentally obtained sample on wetted cotton swab
4. Manure sample inside small diameter tube(s)
5. Placental manure sample inside small diameter tube(s)
6. Blood collected in heparinized glass or plastic capillary tube
7. Blood collected from pipette tip
8. Blood collected and dried onto Qiagen QIAcard
9. Saliva collected on applicator Total DNA from cotton swab and small tube samples was extracted and purified using Qiagen DNeasy Blood & Tissue Kit (Qiagen, Inc., Valencia, Calif.). The suggested manufacturer's protocol "Purification of Total DNA from Animal Blood or Cells (Spin-Column)" was performed. Minor changes were incorporated into the protocol for manure and placental manure samples. For samples containing more than one small tube, the Master Lysis Buffer volume was increased two fold, samples were applied to Spin Columns/Collection Tubes in 2 sequential loading applications (due to increased volume), 8000 rpm spins for 1 minute were increased to 9000 rpm for 3 minutes, and 13600 rpm spin for 3 minutes increased to 6 minutes. Total DNA from cotton swab, small diameter tube, capillary tube, pipette tip, QIAcard (excised 2.5 sq mm), and saliva applicator samples was extracted using Epicentre QuickExtract DNA Extraction Solution (Epicentre Biotechnologies, Madison, Wis.). The suggested manufacturer's protocol was performed with the following changes: for cotton swab and small diameter tube the volume of QE used was 100 uL and for capillary tube, pipette tip, QIAcard, and saliva applicator the volume of QE used was 50 uL. The final solution was diluted 1:4 with DNase free water (Boston BioProducts Inc., Worcester, Mass.). PCR methods including extraction methods and PCR techniques are undergoing rapid developments including advances in instrumentation. The processes described above and below are currently practiced on the inventor's farm. However, these methods should not be considered limiting and advanced PCR techniques can be employed in the overall method described in this patent document.

Appendix "B"

PCR Reaction Conditions

Extracted DNA, oligonucleotide primers, and GoTaq Green Master Mix (Promega Corporation, Madison, Wis.) were mixed together following Promega's suggested protocol for PCR. Mineral oil was added to samples before placing them in PerkinElmer 480 Thermocycler (PerkinElmer, Waltham, Mass.). Basically, the PCR steps included initial denaturation (95° C. for 2 minutes) followed by a 40 cycle loop of denaturation (95° C. for 30 seconds), annealing (see table below), and extension (72° C. for 1 minute), and then final extension (72° C. for 5 minutes) with a hold at 4° C. The following table summarizes primer and PCR conditions:

TABLE 4

| | Multplex GAPDH | GAPDH (uM) | ADV (uM) | Anneal (° C.) | Swab DNA (uL) | Small Tube DNA (uL) | QE DNA:H2O 1:4 (uL) |
|---|---|---|---|---|---|---|---|
| V1a | No | — | 0.1 | 57 | 3 | — | — |
| V2 | No | — | 0.6 | 55 | 5 | — | — |
| V3 | Yes | 0.2 | 0.4 | 57 | 10 | — | — |
| V4 | No | — | 0.1 | 55 | 5 | — | — |
| V4b/V5b | No | — | 0.4 | 57 | 6 | — | — |
| V5 | Yes | 0.2 | 0.4 | 57 | 10 | 5 | 5 |
| V6a | No | — | 0.1 | 57 | 10 | — | — |

Completed PCR reactions were subjected to agarose electrophoresis. PCR products (amplicons) were visualized by UV fluorescence using GelRed Nucleic Acid Stain (Phenix Research Products, Candler, N.C.) incorporated in the agarose. The presence of the GAPDH amplicon (250 bp) in the sample indicated that (cellular) DNA was extracted correctly and PCR performed properly. Appearance of the mADV amplicon (802 bp for V5) indicated the presence of viral DNA in sample.

Appendix "C"

Cleaning/Sanitation

After removal of mink from the area, the first steps in cleaning are described as "dry cleaning" whereupon any remaining feed, manure, and other debris is scrapped from the pens and used bedding materials are removed from the boxes and allowed to fall to the ground. Next the manure, bedding and other materials are removed as much as possible and taken to a compost pile outside and downwind from the ranch. Spreading of this material is not recommended as virus may spread to feral animals and perpetuate the infection outside of the farm. Layering of manure and "quick lime" (Ca0) to this compost pile has been recommended to raise the pH to unfavorable levels for the AD virus to survive.

If boxes are removable from their pens, they are immersed in a 3% NaOH solution as well as any other wooden-ware associated. These are then cleaned typically with a cleaning machine delivering 4 GPM @ 3000 PSI @ 190 degrees F. The outside surfaces of the box are done first finishing with the inside surfaces. Other parts are cleaned similarly whereupon the box with its parts are removed from the shed and immersed in a 500 ppm solution of Oxine (Bio-Cide International, Norman, Okla.) and palletized in a way for air circulation for the natural drying of the Oxine solution from the boxes. Afterward they are stretched wrapped for protection and taken to clean storage until needed.

The next phase of cleaning addresses the wire pens and inside surfaces of the shed. In one method the pens are sprayed with a 3% NaOH solution with the optional addition of a foaming agent to enhance maximum contact to the extremely large surface area involved. While this is soaking, the inside roof and other areas are sprayed with a detergent [Complete Plus, (Camco Chemical, Madison, Wis.)], again with the optional use of a foaming agent. The 3% NaOH solution is not recommended on surfaces that are aluminum such as shed roofs so the use of a detergent is used instead. Rinsing of the inner roof surface and other structural parts of the shed is preformed with the same machine initially before the wire pens are done working in a top to bottom fashion. The pens are carefully rinsed in a manner that directs the spray to as many angles possible to minimize shadowed areas formed by the spraying action. The pens are then sprayed with a 500 ppm solution of Oxine and allowed to air dry. Again the addition of a foaming agent enhances the contact time and completeness of the sanitizing solution. The final step of preparing the shed is to broadcast CaO inside and outside of the shed by use of a garden pulled lawn broadcaster. The CaO is applied at the rate of approximately six pounds per square yard. The shed remains in this state until just prior to moving in PCR mADV negative animals. At that time, immediately before the shed is utilized, a second application of 500 ppm Oxine is applied to the pens to ensure sanitation before use. Under all circumstances, strict ranch hygiene is absolutely essential for the successful implementation of eradication of the disease. Animal testing alone will not ensure elimination of a pathogen without adherence to the highest levels of biosecurity.

Appendix "D"

Blood Collection Process for Antibody (ELISA or LFIA) and PCR Testing

To minimize the transmission of the disease during this procedure, a technique of using Oxine soaked handling gloves is employed as to provide a sanitizing surface for any bodily fluids from the animals to be neutralized upon contact. The gloves are soaked in a 500 ppm solution of Oxine until saturated and the handler first dawns a pair of latex gloves before the soaked catching gloves to protect his/her hands from the long term exposure to the Oxine solution. The mink are carefully caught as to avoid contact of the rear feet with the Oxine laden gloves as it was discovered that Oxine will produce a false positive reaction on LFIA test strips when incorporated with the blood sample (personal communication).

The handler holds the animal horizontal with the rear feet to him/her and extended beyond the pen with the fore feet placed firmly on the top part of the pen while gently rolling the animal to the left side to raise the right rear foot upward. The sampling person prepares to acquire the blood sample. Since a third hand is required, the mouth of the sampler may be used to hold the stem ends of the sterile cotton swabs while the right hand holds the clippers and is the only hand used to open and close sample containers. Reproducible non-cross contaminating sample acquisition is crucial at this stage. It is imperative that the sampler maintains a clean hand, usually the most dexterous one, and a sampling hand, one that is in repetitive physical contact with the animals. The two hands never exchange duties and maintain their respective operations.

The technique of blood collection is best preformed as follows. With the left hand, the sampler firmly grabs the elevated right rear foot of the mink such that the foot pad rests completely on the left thumb of the sampler. With the right hand, the sampler skillfully clips a toenail, preferably from the smallest, last digit, just above the quick line with a small pair of toenail clippers maintaining the grip with his left thumb and left fore finger of the left hand. Blood will flow momentarily or, if not, a second clipping may be required or a slight relaxation of the grip may allow the flow of blood to proceed. The sampler removes from his mouth a sterile cotton swab with his clean right hand and acquires first the sample for blood LFIA. The stem of the swab is transferred to the released left hand, the pre-labeled sample container lid is opened with the thumb and fore finger of the right hand and the cotton head of the blood soaked swab is cut with the clippers still held in the right hand just above the cotton head. The lid is closed with the right thumb and fore finger. The stem of the swab is discarded with the left hand and is then used to re-grip the animal's right rear foot as before. Secondly, the sample for blood PCR is acquired in the same fashion excluding any contact with anything other than free flowing blood from the toenail to avoid environmental virus contamination. This process is repeated using the same hands in the same fashion as previously described. Upon completion of acquiring samples from the animal, the clippers are wiped free of any blood with a paper towel using the left hand and exchanged with a second pair of clippers soaking in 500 ppm of Oxine. This second pair is carefully dried with a clean portion of paper towel using the left hand but not allowing the sampling fingers to touch any part of the clipper's cutting surface. Layers of clean towel are maintained between the left fingers and cutting surface and the handles are held by the right hand. The purpose of this drying action is to eliminate false positive LFIA that may arise with Oxine present in the blood sample. In practice, the used towel is not discarded until used to remove blood from the next clipping action prior to immersion in Oxine. A fresh towel is only used for the pair of clippers immediately removed from the Oxine.

Blood collection can also be taken using 1.0 to 1.1 mm ID Na heparinized plastic capillary tubes commonly used in CIEP (counterimmunoelectrophoresis) testing, (Globe Scientific, Paramus, N.J.). The mink is similarly handled and hygiene observed as above only the use of a capillary tube instead of cotton swab acquires the sample. By this method, volumes of samples can be accurately established due to the constant capillary diameter and length of tube filled. For instance a half-filled capillary tube is approximately 35 uL in volume. In some sampling procedures, the contents of the capillary tube are expelled by the use of a capillary bulb into a pre-labeled/bar coded sampling vial with a snap top or into a pre-labeled/bar coded 48 or 96 well plate suitable for extraction and/or PCR.

Yet another collection process that has been successfully used is the spotting, spreading, and drying of a drop of blood onto a QIAcard (QIAGEN, Valencia, Calif.) and is useful for sample archiving. Punched out portion of the dried, spotted area yields sufficient sample for analysis and it has been found that cross-contamination is not a factor to be considered by the protocol outlined by the manufacturer. Samples are stored at −20° C. until ready for testing for PCR and LFIA samples are stored at 4° C. until testing.

Appendix "E"

Environmental Collection Process for PCR

Unlike other testing methods currently available, the use of PCR technology allows testing of the environment for mADV presence. This is particularly important to eliminate the possibility of recontamination of the animals that are returned to the pens. Thus, environmental sampling is most useful after a cleaning procedure to determine the efficacy of the cleaning and sanitizing processes. Typically the method used is as follows. An area to be investigated is aggressively rubbed with a cotton swab that has been soaked in a Phosphate Buffered Saline (PBS, Boston BioProducts, Inc., Worcester, Mass.). The presoaking of the cotton swab aids in the acquisition and preservation of the sample. The sampling area can include, but is not limited to, the wire cages, wooden boxes and their parts, inside of the housing roof surfaces, and the ground to name a few of the more obvious and worthwhile sites. As previously stated, the use of proper hygiene while manipulating the sample is always important. The sample may be stored at 4° C. until the PCR process.

We claim:

1. A non-invasive, non-tactile method for determining in minks whether one or more mink offspring and female parent are infected with Aleutian disease virus (mADV), comprising the following steps:

a) obtaining a birthing manure sample from the female after consumption by the female of the placentas of her offspring;

b) extracting DNA from the manure sample; and c) assaying the DNA from the birthing manure sample for mADV using PCR amplification performed with one or more of the following primer sets, or their complementary sets, or sets having at least 85% homology thereto: SEQ ID NO: 7 and SEQ ID NO: 8; SEQ ID NO: 9 and SEQ ID NO: 10; SEQ ID NO: 11 and SEQ ID NO: 12 wherein detection of mADV indicates infection of one or more of the offspring and/or the female.

2. The method of claim 1 in which the manure sample is taken after the first elimination after the female mink has consumed the placentas.

3. In a mink population in which previous tests of the females using a PCR assay that detects mADV did not indicate the presence of the virus, a non-invasive, non-tactile method for determining whether a female is a non-permissive carrier of the virus comprising the following steps:

a) obtaining a birthing manure sample from the female after consumption by the female of the placentas of her offspring;

b) extracting DNA from the manure sample; and c) assaying the DNA from the birthing manure sample for mADV using PCR amplification performed with one or more of the following primer sets, or their complementary sets, or sets having at least 85% homology thereto:

SEQ ID NO: 7 and SEQ ID NO: 8; SEQ ID NO: 9 and SEQ ID NO: 10; SEQ ID NO: 11 and SEQ ID NO: 12 wherein detection of mADV indicates infection of one or more of the offspring and that the female parent is a non-permissive carrier for the virus.

4. In a mink population in which previous tests of the females using a PCR assay that detects mADV did not indicate the presence of the virus, a non-invasive, non-tactile method for determining whether a female is a non-permissive carrier of the mADV virus which she can pass off to her offspring comprising the following steps:

a) obtaining a birthing manure sample from the female after consumption by the female of the placentas of her offspring;

b) extracting DNA from the manure sample; and c) assaying the DNA from the birthing manure sample for mADV using PCR amplification performed with one or more of the following primer sets, or their complementary sets, or sets having at least 85% homology thereto: SEQ ID NO: 7 and SEQ ID NO: 8; SEQ ID NO: 9 and SEQ ID NO: 10; SEQ ID NO: 11 and SEQ ID NO: 12 wherein detection of mADV indicates infection of one or more of the offspring and that the female parent is a non-permissive carrier for the virus;

d) determining which of the offspring of a non-permissive parent is infected with the mADV virus or are non-permissive carriers of the virus comprising:

1) obtaining blood or saliva samples of each offspring;

2) extracting DNA from the blood or saliva samples; and 3) assaying the DNA from the blood or saliva samples for mADV using PCR amplification performed with one or more of the following primer sets, or their complementary sets, or sets having at least 85% homology thereto: SEQ ID NO: 7 and SEQ ID NO: 8; SEQ ID NO: 9 and SEQ ID NO: 10; and SEQ ID NO: 11 and SEQ ID NO: 12 wherein detection of mADV indicates infection of an offspring and no detection of mADV indicates that the offspring may be a non-permissive carrier of the virus.

5. A non-invasive, non-tactile method for effectively screening a large number of minks to determine whether one or more offspring and/or female parent are infected with mADV, comprising the following steps:

a) combining birthing manure samples from several females after consumption by the females of the placentas of their offspring;

b) extracting DNA from the combined manure sample; and c) assaying the DNA from the combined birthing manure sample for mADV using PCR amplification performed with one or more of the following primer sets, or their complementary sets, or sets having at least 85% homology thereto: SEQ ID NO: 7 and SEQ ID NO: 8; SEQ ID NO: 9 and SEQ ID NO: 10; SEQ ID NO: 11and SEQ ID NO: 12 wherein detection of mADV indicates infection of one or more of the offspring and/or female parents.

6. A non-invasive, non-tactile method for identifying from among a large number of female minks those that are infected with mADV, comprising the following steps:

a) combining birthing manure samples from several females after consumption by the females of the placentas of their offspring;

b) extracting DNA from the combined manure sample; and c) assaying the DNA from the combined birthing manure sample for mADV using PCR amplification performed with one or more of the following primer sets, or their complementary sets, or sets having at least 85% homology thereto: SEQ ID NO: 7 and SEQ ID NO: 8; SEQ ID NO: 9 and SEQ ID NO: 10; SEQ ID NO: 11and SEQ ID NO: 12 wherein detection of mADV indicates infection of one or more of the offspring and/or female parents;

d) determining the infected or non-infected status of each female mink whose manure was included in the combined birthing manure sample found to contain the mADV virus comprising the following steps:

1) obtaining blood or saliva samples of each female parent;

2) extracting DNA from the blood or saliva samples and 3) assaying the DNA from the blood and saliva samples for mADV using PCR amplification performed with one or more of the following primer sets, or their complementary sets, or sets having at least 85% homology thereto: SEQ ID NO: 7 and SEQ ID NO: 8; SEQ ID NO: 9 and SEQ ID NO: 10; SEQ ID NO: 11 and SEQ ID NO: 12 wherein detection of mADV indicates infection of the female mink from which the sample was taken.

7. A non-invasive, non-tactile method for determining in minks whether one or more mink offspring and female parent are infected with Aleutian disease virus (mADV), comprising the following steps:

a) obtaining a birthing manure sample from the female after consumption by the female of the placentas of her offspring;

b) extracting DNA from the manure sample; and c) assaying the DNA from the birthing manure sample for mADV using PCR amplification performed with one or more of the following primer sets, or their complementary sets, or sets having at least 85% homology thereto: SEQ ID NO: 1 and SEQ ID NO: 2; SEQ ID NO: 3 and SEQ ID NO: 4; SEQ ID NO: 5 and SEQ ID NO: 6; SEQ ID NO: 13 and SEQ ID NO: 14 wherein detection of mADV indicates infection of one or more of the offspring and/or the female.

8. In a mink population in which previous tests of the females using a PCR assay that detects mADV did not indicate the presence of the virus, a non-invasive, non-tacticle method for determining whether a female is a non-permissive carrier of the virus comprising the following steps:

a) obtaining a birthing manure sample from the female after consumption by the female of the placentas of her offspring;

b) extracting DNA from the manure sample; and c) assaying the DNA from the birthing manure sample for mADV using PCR amplification performed with one or more of the following primer sets, or their complementary sets, or sets having at least 85% homology thereto: SEQ ID NO: 1 and SEQ ID NO: 2; SEQ ID NO: 3 and SEQ ID NO: 4; SEQ ID NO: 5 and SEQ ID NO: 6; SEQ ID NO: 13 and SEQ ID NO: 14 wherein detection of mADV indicates infection of one or more of the offspring and that the female parent is a non-permissive carrier for the virus.

9. In a mink population in which previous tests of the females using a PCR assay that detects mADV did not indicate the presence of the virus, a non-invasive, non-tactile method for determining whether a female is a non-permissive carrier of the mADV virus which she can pass off to her offspring comprising the following steps:

a) obtaining a birthing manure sample from the female after consumption by the female of the placentas of her offspring;

b) extracting DNA from the manure sample; and c) assaying the DNA from the birthing manure sample for mADV using PCR amplification performed with one or more of the following primer sets, or their complementary sets, or sets having at least 85% homology thereto: SEQ ID NO: 1 and SEQ ID NO: 2; SEQ ID NO: 3 and SEQ ID NO: 4; SEQ ID NO: 5 and SEQ ID NO: 6; SEQ ID NO: 13 and SEQ ID NO: 14 wherein detection of mADV indicates infection of one or more of the offspring and that the female parent is a non-permissive carrier for the virus;

d) determining which of the offspring of a non-permissive parent is infected with the mADV virus or are non-permissive carriers of the virus comprising:

1) obtaining blood or saliva samples of each offspring;

2) extracting DNA from the blood or saliva samples; and 3) assaying the DNA from the blood or saliva samples for mADV using PCR amplification performed with one or more of the following primer sets, or their complementary sets, or sets having at least 85% homology thereto: SEQ ID NO: 1 and SEQ ID NO: 2; SEQ ID NO: 3 and SEQ ID NO: 4; SEQ ID NO: 5 and SEQ ID NO: 6; SEQ ID NO: 13 and SEQ ID NO: 14 wherein detection of mADV indicates infection of an offspring and no detection of mADV indicates that the offspring may be a non-permissive carrier of the virus.

10. A non-invasive, non-tactile method for identifying from among a large number of female minks those that are infected with mADV, comprising the following steps:

a) combining birthing manure samples from several females after consumption by the females of the placentas of their offspring;

b) extracting DNA from the combined manure sample; and c) assaying the DNA from the combined birthing manure sample for mADV using PCR amplification performed with one or more of the following primer sets, or their complementary sets, or sets having at least 85% homology thereto: SEQ ID NO: 1 and SEQ ID NO: 2; SEQ ID NO: 3 and SEQ ID NO: 4; SEQ ID NO: 5 and SEQ ID NO: 6; SEQ ID NO: 13 and SEQ ID NO: 14 wherein detection of mADV indicates infection of one or more of the offspring and/or female parents;

d) determining the infected or non-infected status of each female mink whose manure was included in the combined birthing manure sample found to contain the mADV virus comprising the following steps:

1) obtaining blood or saliva samples of each female parent;

2) extracting DNA from the blood or saliva samples; and 3) assaying the DNA from the blood and saliva samples for mADV using PCR amplification performed with one or more of the following primer sets, or their complementary sets, or sets having at least 85% homology thereto: SEQ ID NO: 1 and SEQ ID NO: 2; SEQ ID NO: 3 and SEQ ID NO: 4; SEQ ID NO: 5 and SEQ ID NO: 6; SEQ ID NO: 13 and SEQ ID NO: 14 wherein detection of mADV indicates infection of the female mink from which the sample was taken.

11. A non-invasive, non-tactile method for effectively screening a large number of minks to determine whether one or more offspring and/or female parent are infected with mADV, comprising the following steps:

a) combining birthing manure samples from several females after consumption by the females of the placentas of their offspring;

b) extracting DNA from the combined manure sample; and c) assaying the DNA from the combined birthing manure sample for mADV using PCR amplification performed with one or more of the following primer sets, or their complementary sets, or sets having at least 85% homology thereto: SEQ ID NO: 1 and SEQ ID NO: 2; SEQ ID NO: 3 and SEQ ID NO: 4; SEQ ID NO: 5 and SEQ ID NO: 6; SEQ ID NO: 13 and SEQ ID NO: 14 wherein detection of mADV indicates infection of one or more of the offspring and/or female parents.

* * * * *